(12) United States Patent
Welsh et al.

(10) Patent No.: US 7,662,388 B2
(45) Date of Patent: Feb. 16, 2010

(54) ENDOGENOUS PEPTIDE AND ACTIVE SUBFRAGMENTS THEREOF

(75) Inventors: Lena Claesson Welsh, Uppsala (SE); Anna-Karin Olsson, Uppsala (SE)

(73) Assignee: Innoventus Project AB, Uppsala (SE)

( * ) Notice: Subject to any disclaimer, the term of this patent is extended or adjusted under 35 U.S.C. 154(b) by 314 days.

(21) Appl. No.: 10/563,389

(22) PCT Filed: Jul. 5, 2004

(86) PCT No.: PCT/SE2004/001091

§ 371 (c)(1),
(2), (4) Date: Feb. 15, 2007

(87) PCT Pub. No.: WO2005/003162

PCT Pub. Date: Jan. 13, 2005

(65) Prior Publication Data

US 2008/0125355 A1     May 29, 2008

Related U.S. Application Data

(60) Provisional application No. 60/485,185, filed on Jul. 7, 2003.

(30) Foreign Application Priority Data

Jul. 7, 2003   (SE)   .................................... 0301988

(51) Int. Cl.
    *A61K 39/00*   (2006.01)
    *A61K 38/00*   (2006.01)
    *A61K 38/04*   (2006.01)
(52) U.S. Cl. ..................... 424/184.1; 424/185.1; 514/2; 530/324; 530/325; 530/326; 530/327; 530/328; 530/329; 530/330
(58) Field of Classification Search ........................ None
See application file for complete search history.

(56) References Cited

U.S. PATENT DOCUMENTS

| 7,205,392 | B2 * | 4/2007 | Olsson et al. ................ 530/395 |
| 7,294,515 | B2 * | 11/2007 | Hutchens et al. ............ 436/174 |
| 7,563,765 | B2 * | 7/2009 | Olsson et al. ................... 514/9 |
| 2001/0041670 | A1 | 11/2001 | Simantov et al. | |
| 2005/0042201 | A1 * | 2/2005 | Olsson et al. ............... 424/85.7 |

FOREIGN PATENT DOCUMENTS

| WO | WO02/064621 | 8/2002 |
| WO | WO02/076486 | 10/2002 |
| WO | WO03/077872 | 9/2003 |

OTHER PUBLICATIONS

J.C. Juarez, et al. "Histidine-proline-rich Glycoprotein has potent antiangiogenic activity mediated through the histidine-proline domain" *Cancer Research* vol. 62 (Sep. 15, 2002), pp. 5344-5350.

R. Simantov, et al. "Histidine-rich glycoprotein inhibits the antiagiogenic effect of thrombospondin-1" *The Journal of Clinical Investigation* (Jan. 2001) vol. 107 (1), pp. 45-52.

A. Olsson, et al. "A fragment of histidine-rich glycoprotein is a potent inhibitor of tumor vascularization" *Cancer Research* vol. 64 (2004) pp. 599-605.

Hulett M.D., et al. "Murine histidide-rich glycoprotein: Cloning, characterization and cellular origin" *Immunology and Cell Biology* (2000) 78, pp. 280-287.

D. J. Borza, et al. "Domain structure and conformation of histidine-roline-rich glycoprotein" *Biochemistry* (1996) vol. 35, pp. 1925-1934.

T. Kolde, et al. "Amino Acid Sequence of Human Histidine-Rich Glycoprotein Derived from the Nucleotide Sequence of its cDNA" *Biochemistry* vol. 25 (1986), pp. 2220-2225.

H.K. Lunen, et al. "Interaction of Heparin with Histidine-rich Glycoprotein" *Annals New York Academy of Sciences* vol. 556 (1985), pp. 181-185.

Borza and Morgan, "Histidine-Proline-rich Glycoprotein as a Plasma pH Sensor," *J. Biol. Chem.*, 1998, 273(10):5493-5499.

Borza and Morgan, "Acceleration of Plasminogen Activation by Tissue Plasminogen Activator on Surface-bound Histidine-proline-rich Glycoprotein," *J. Biol. Chem.*, 1997, 272(8):5718-5726.

Brown and Parish, "Histidine-Rich Glycoprotein and Platelet Factor 4 Mask Heparan Sulfate Proteoglycans Recognized by Acidic and Basic Fibroblast Growth Factor," *Biochem.*, 1994, 33:13918-13927.

Carmeliet and Jain, "Angiogenesis in cancer and other diseases," *Nature*, 2000, 407:249-257.

Folkman, "Angiogenesis in cancer, vascular, rheumatoid and other disease," *Nature Med.*, 1995, 1(1):27-31.

Gorgani et al., "Histidine-Rich Glycoprotein Binds to Human IgG and C1q and Inhibits the Formation of Insoluble Immune Complexes," *Biochem.*, 1997, 36:6653-6662.

Gorgani et al., "Histidine-Rich Glycoprotein Binds to DNA and FcγRI and Potentiates the Ingestion of Apoptotic Cells by Macrophages," *J. Immunol.*, 2002, 169:4745-4751.

Gura, "Cancer Models: Systems for Identifying New Drugs Are Often Faulty," *Science*, 1997, 278:1041-1042.

Hawighorst et al., "Activation of the Tie2 Receptor by Angiopoietin-1 Enhances Tumor Vessel Maturation and Impairs Squamous Cell Carcinoma Growth," *Am. J. Pathol.*, 2002, 160(4):1381-1392.

Kerbel, "Tumor angiogenesis: past, present and the near future," *Carcinogenesis*, 2000, 21(3):505-515.

(Continued)

*Primary Examiner*—Maher M Haddad
(74) *Attorney, Agent, or Firm*—Fish & Richardson P.C.

(57) ABSTRACT

The present invention relates to a substantially pure biologically active consecutive anti-angiogenic polypeptide comprising the central region of human Histidine Rich Glycoprotein (HRGP). Said polypeptide is shown to comprise a potential endogenous, naturally occurring subfragment of human HRGP, comprising similar anti-angiogenic activities as the mature protein. The present invention also relates to one or more new biologically active subfragments of human HRGP, derived from said central region. Said subfragments are all characterized by having anti-angiogenic activity. One of the active subfragments is referred to as Pep2. Enscoped by the present invention are also anti-angiogenic subfragments derived from Pep2, one of them comprising a newly identified presently minimal functional entity.

26 Claims, 16 Drawing Sheets

OTHER PUBLICATIONS

Figure 1:
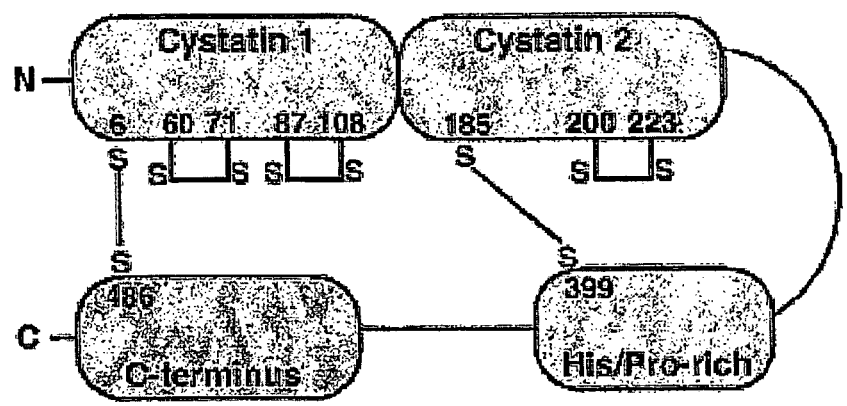
Figure 1:
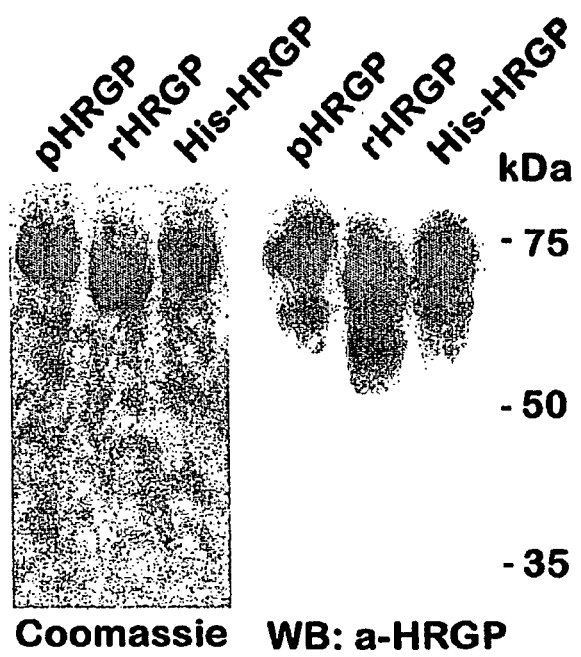
Figure 1:

Koide et al., "The heparin-binding site(s) of histidine-rich glycoprotein as suggested by sequence homology with antithrombin III," *FEBS*, 1986, 194(2):242-244.

Kluszynski et al., "Zinc as a Cofactor for Heparin Neutralization by Histidine-rich Glycoprotein," *J. Biol. Chem.*, 1997, 272(21):13541-13547.

Lamb-Wharton and Morgan, "Induction of T-Lymphocyte Adhesion by Histidine-Proline-Rich Glycoprotein and Concanavalin A," *Cell. Immunol.*, 1993, 152:544-555.

Lijnen et al., "Heparain Binding Properties of Human Histidine-rich Glycoprotein. Mechanism and Role in the Neutralization of Heparin in Plasma," *J. Biol. Chem.*, 1983, 258(6):3803-3808.

Olsen et al., "Histidine-rich glycoprotein binding to T-cell lines and its effect on T-cell substratum adhesion is strongly potentiated by zinc," *Immunology*, 1996, 88:198-206.

Peterson et al., "Histidine-rich Glycoprotein Modulation of the Anticoagulant Activity of Heparin," *J. Biol. Chem.*, 1987, 262(16):7567-7574.

Simon et al., "Peptoids: a modular approach to drug discovery," *Proc. Natl. Acad. Sci. USA*, 1992, 89:9367-9371.

Zhang et al. "Two-chain high molecular weight kininogen induces endothelial cell apoptosis and inhibits angiogenesis: partial activity within domain 5," *FASEB J.*, 2000, 14:2589-2600.

Wassberg et al., "Inhibition of Angiogenesis Induces Chromaffin Differentiation and Apoptosis in Neuroblastoma," *Am. J. Pathol.*, 1999, 154(2):395-403.

* cited by examiner

A:

B:

C:

A:

B:

A:

SEQUENCE LISTING

<160> NUMBER OF SEQ ID NOS: 31

<210> SEQ ID NO 1
<211> LENGTH: 35
<212> TYPE: PRT
<213> ORGANISM: Homo sapiens

<400> SEQUENCE: 1

Asp Leu His Pro His Lys His His Ser His Glu Gln His Pro His Gly
 1               5                  10                  15

His His Pro His Ala His His Pro His Glu His Asp Thr His Arg Gln
                20                  25                  30

His Pro His
        35

<210> SEQ ID NO 2
<211> LENGTH: 151
<212> TYPE: PRT
<213> ORGANISM: Homo sapiens

<400> SEQUENCE: 2

His Leu Gly His Pro Phe His Trp Gly Gly His Glu Arg Ser Ser Thr
 1               5                  10                  15

Thr Lys Pro Pro Phe Lys Pro His Gly Ser Arg Asp His His His Pro
                20                  25                  30

His Lys Pro His Glu His Gly Pro Pro Pro Pro Asp Glu Arg Asp
            35                  40                  45

His Ser His Gly Pro Pro Leu Pro Gln Gly Pro Pro Pro Leu Leu Pro
        50                  55                  60

Met Ser Cys Ser Cys Gln His Ala Thr Phe Gly Thr Asn Gly Ala
 65                 70                  75                  80

Gln Arg His Ser His Asn Asn Asn Ser Ser Asp Leu His Pro His Lys
                85                  90                  95

His His Ser His Glu Gln His Pro His Gly His His Pro His Ala His
                100                 105                 110

His Pro His Glu His Asp Thr His Arg Gln His Pro His Gly His His
            115                 120                 125

Pro His Gly His His Pro His Gly His His Pro His Gly His His Pro
        130                 135                 140

His Gly His His Pro His Cys
145                 150

<210> SEQ ID NO 3
<211> LENGTH: 507

<212> TYPE: PRT
<213> ORGANISM: Homo sapiens

<400> SEQUENCE: 3

```
Val Ser Pro Thr Asp Cys Ser Ala Val Glu Pro Glu Ala Glu Lys Ala
  1               5                  10                  15

Leu Asp Leu Ile Asn Lys Arg Arg Arg Asp Gly Tyr Leu Phe Gln Leu
             20                  25                  30

Leu Arg Ile Ala Asp Ala His Leu Asp Arg Val Glu Asn Thr Thr Val
         35                  40                  45

Tyr Tyr Leu Val Leu Asp Val Gln Glu Ser Asp Cys Ser Val Leu Ser
 50                  55                  60

Arg Lys Tyr Trp Asn Asp Cys Glu Pro Pro Asp Ser Arg Arg Pro Ser
 65                  70                  75                  80

Glu Ile Val Ile Gly Gln Cys Lys Val Ile Ala Thr Arg His Ser His
                 85                  90                  95

Glu Ser Gln Asp Leu Arg Val Ile Asp Phe Asn Cys Thr Thr Ser Ser
            100                 105                 110

Val Ser Ser Ala Leu Ala Asn Thr Lys Asp Ser Pro Val Leu Ile Asp
        115                 120                 125

Phe Phe Glu Asp Thr Glu Arg Tyr Arg Lys Gln Ala Asn Lys Ala Leu
130                 135                 140

Glu Lys Tyr Lys Glu Glu Asn Asp Asp Phe Ala Ser Phe Arg Val Asp
145                 150                 155                 160

Arg Ile Glu Arg Val Ala Arg Val Arg Gly Gly Glu Gly Thr Gly Tyr
                165                 170                 175

Phe Val Asp Phe Ser Val Arg Asn Cys Pro Arg His His Phe Pro Arg
            180                 185                 190

His Pro Asn Val Phe Gly Phe Cys Arg Ala Asp Leu Phe Tyr Asp Val
        195                 200                 205

Glu Ala Leu Asp Leu Glu Ser Pro Lys Asn Leu Val Ile Asn Cys Glu
210                 215                 220

Val Phe Asp Pro Gln Glu His Glu Asn Ile Asn Gly Val Pro Pro His
225                 230                 235                 240

Leu Gly His Pro Phe His Trp Gly Gly His Glu Arg Ser Ser Thr Thr
                245                 250                 255

Lys Pro Pro Phe Lys Pro His Gly Ser Arg Asp His His His Pro His
            260                 265                 270

Lys Pro His Glu His Gly Pro Pro Pro Asp Glu Arg Asp His
        275                 280                 285

Ser His Gly Pro Pro Leu Pro Gln Gly Pro Pro Leu Leu Pro Met
290                 295                 300

Ser Cys Ser Ser Cys Gln His Ala Thr Phe Gly Thr Asn Gly Ala Gln
305                 310                 315                 320

Arg His Ser His Asn Asn Ser Ser Asp Leu His Pro His Lys His
                325                 330                 335

His Ser His Glu Gln His Pro His Gly His Pro His Ala His His
            340                 345                 350

Pro His Glu His Asp Thr His Arg Gln His Pro His Gly His His Pro
        355                 360                 365

His Gly His His Pro His Gly His Pro His Gly His His Pro His
370                 375                 380

Gly His His Pro His Cys His Asp Phe Gln Asp Tyr Gly Pro Cys Asp
385                 390                 395                 400
```

-continued

```
Pro Pro Pro His Asn Gln Gly His Cys Cys His Gly His Gly Pro Pro
                405                 410                 415
Pro Gly His Leu Arg Arg Gly Pro Gly Lys Gly Pro Arg Pro Phe
        420                 425                 430
His Cys Arg Gln Ile Gly Ser Val Tyr Arg Leu Pro Pro Leu Arg Lys
    435                 440                 445
Gly Glu Val Leu Pro Leu Pro Glu Ala Asn Phe Pro Ser Phe Pro Leu
450                 455                 460
Pro His His Lys His Pro Leu Lys Pro Asp Asn Gln Pro Phe Pro Gln
465                 470                 475                 480
Ser Val Ser Glu Ser Cys Pro Gly Lys Phe Lys Ser Gly Phe Pro Gln
                485                 490                 495
Val Ser Met Phe Phe Thr His Thr Phe Pro Lys
                500                 505

<210> SEQ ID NO 4
<211> LENGTH: 25
<212> TYPE: PRT
<213> ORGANISM: Homo sapiens

<400> SEQUENCE: 4

Gly His His Pro His Gly His His Pro His Gly His His Pro His Gly
 1               5                  10                  15
His His Pro His Gly His His Pro His
                20                  25

<210> SEQ ID NO 5
<211> LENGTH: 25
<212> TYPE: PRT
<213> ORGANISM: Homo sapiens

<400> SEQUENCE: 5

His His His His His His His His His His His His His His His His
 1               5                  10                  15
His His His His His His His His His
                20                  25

<210> SEQ ID NO 6
<211> LENGTH: 240
<212> TYPE: PRT
<213> ORGANISM: Homo sapiens

<400> SEQUENCE: 6

Val Ser Pro Thr Asp Cys Ser Ala Val Glu Pro Glu Ala Glu Lys Ala
 1               5                  10                  15
Leu Asp Leu Ile Asn Lys Arg Arg Arg Asp Gly Tyr Leu Phe Gln Leu
                20                  25                  30
Leu Arg Ile Ala Asp Ala His Leu Asp Arg Val Glu Asn Thr Thr Val
            35                  40                  45
Tyr Tyr Leu Val Leu Asp Val Gln Glu Ser Asp Cys Ser Val Leu Ser
        50                  55                  60
Arg Lys Tyr Trp Asn Asp Cys Glu Pro Pro Asp Ser Arg Arg Pro Ser
65                  70                  75                  80
Glu Ile Val Ile Gly Gln Cys Lys Val Ile Ala Thr Arg His Ser His
                85                  90                  95
Glu Ser Gln Asp Leu Arg Val Ile Asp Phe Asn Cys Thr Thr Ser Ser
            100                 105                 110
```

Val Ser Ser Ala Leu Ala Asn Thr Lys Asp Ser Pro Val Leu Ile Asp
            115                 120                 125

Phe Phe Glu Asp Thr Glu Arg Tyr Arg Lys Gln Ala Asn Lys Ala Leu
130                 135                 140

Glu Lys Tyr Lys Glu Glu Asn Asp Asp Phe Ala Ser Phe Arg Val Asp
145                 150                 155                 160

Arg Ile Glu Arg Val Ala Arg Val Arg Gly Gly Glu Gly Thr Gly Tyr
                165                 170                 175

Phe Val Asp Phe Ser Val Arg Asn Cys Pro Arg His His Phe Pro Arg
            180                 185                 190

His Pro Asn Val Phe Gly Phe Cys Arg Ala Asp Leu Phe Tyr Asp Val
            195                 200                 205

Glu Ala Leu Asp Leu Glu Ser Pro Lys Asn Leu Val Ile Asn Cys Glu
        210                 215                 220

Val Phe Asp Pro Gln Glu His Glu Asn Ile Asn Gly Val Pro Pro His
225                 230                 235                 240

<210> SEQ ID NO 7
<211> LENGTH: 320
<212> TYPE: PRT
<213> ORGANISM: Homo sapiens

<400> SEQUENCE: 7

Val Ser Pro Thr Asp Cys Ser Ala Val Glu Pro Glu Ala Glu Lys Ala
  1               5                  10                  15

Leu Asp Leu Ile Asn Lys Arg Arg Arg Asp Gly Tyr Leu Phe Gln Leu
                20                  25                  30

Leu Arg Ile Ala Asp Ala His Leu Asp Arg Val Glu Asn Thr Thr Val
            35                  40                  45

Tyr Tyr Leu Val Leu Asp Val Gln Glu Ser Asp Cys Ser Val Leu Ser
        50                  55                  60

Arg Lys Tyr Trp Asn Asp Cys Glu Pro Pro Asp Ser Arg Arg Pro Ser
65                  70                  75                  80

Glu Ile Val Ile Gly Gln Cys Lys Val Ile Ala Thr Arg His Ser His
                85                  90                  95

Glu Ser Gln Asp Leu Arg Val Ile Asp Phe Asn Cys Thr Thr Ser Ser
            100                 105                 110

Val Ser Ser Ala Leu Ala Asn Thr Lys Asp Ser Pro Val Leu Ile Asp
        115                 120                 125

Phe Phe Glu Asp Thr Glu Arg Tyr Arg Lys Gln Ala Asn Lys Ala Leu
130                 135                 140

Glu Lys Tyr Lys Glu Glu Asn Asp Asp Phe Ala Ser Phe Arg Val Asp
145                 150                 155                 160

Arg Ile Glu Arg Val Ala Arg Val Arg Gly Gly Glu Gly Thr Gly Tyr
                165                 170                 175

Phe Val Asp Phe Ser Val Arg Asn Cys Pro Arg His His Phe Pro Arg
            180                 185                 190

His Pro Asn Val Phe Gly Phe Cys Arg Ala Asp Leu Phe Tyr Asp Val
            195                 200                 205

Glu Ala Leu Asp Leu Glu Ser Pro Lys Asn Leu Val Ile Asn Cys Glu
        210                 215                 220

Val Phe Asp Pro Gln Glu His Glu Asn Ile Asn Gly Val Pro Pro His
225                 230                 235                 240

Leu Gly His Pro Phe His Trp Gly Gly His Glu Arg Ser Ser Thr Thr
                245                 250                 255

```
Lys Pro Pro Phe Lys Pro His Gly Ser Arg Asp His His Pro His
            260                 265                 270

Lys Pro His Glu His Gly Pro Pro Pro Asp Glu Arg Asp His
        275                 280                 285

Ser His Gly Pro Pro Leu Pro Gln Gly Pro Pro Leu Leu Pro Met
    290                 295                 300

Ser Cys Ser Ser Cys Gln His Ala Thr Phe Gly Thr Asn Gly Ala Gln
305                 310                 315                 320

<210> SEQ ID NO 8
<211> LENGTH: 390
<212> TYPE: PRT
<213> ORGANISM: Homo sapiens

<400> SEQUENCE: 8

Val Ser Pro Thr Asp Cys Ser Ala Val Glu Pro Glu Ala Glu Lys Ala
 1               5                  10                  15

Leu Asp Leu Ile Asn Lys Arg Arg Asp Gly Tyr Leu Phe Gln Leu
            20                  25                  30

Leu Arg Ile Ala Asp Ala His Leu Asp Arg Val Glu Asn Thr Thr Val
        35                  40                  45

Tyr Tyr Leu Val Leu Asp Val Gln Glu Ser Asp Cys Ser Val Leu Ser
    50                  55                  60

Arg Lys Tyr Trp Asn Asp Cys Glu Pro Pro Asp Ser Arg Arg Pro Ser
65                  70                  75                  80

Glu Ile Val Ile Gly Gln Cys Lys Val Ile Ala Thr Arg His Ser His
                85                  90                  95

Glu Ser Gln Asp Leu Arg Val Ile Asp Phe Asn Cys Thr Thr Ser Ser
            100                 105                 110

Val Ser Ser Ala Leu Ala Asn Thr Lys Asp Ser Pro Val Leu Ile Asp
        115                 120                 125

Phe Phe Glu Asp Thr Glu Arg Tyr Arg Lys Gln Ala Asn Lys Ala Leu
    130                 135                 140

Glu Lys Tyr Lys Glu Glu Asn Asp Asp Phe Ala Ser Phe Arg Val Asp
145                 150                 155                 160

Arg Ile Glu Arg Val Ala Arg Val Arg Gly Gly Glu Gly Thr Gly Tyr
                165                 170                 175

Phe Val Asp Phe Ser Val Arg Asn Cys Pro Arg His His Phe Pro Arg
            180                 185                 190

His Pro Asn Val Phe Gly Phe Cys Arg Ala Asp Leu Phe Tyr Asp Val
        195                 200                 205

Glu Ala Leu Asp Leu Glu Ser Pro Lys Asn Leu Val Ile Asn Cys Glu
    210                 215                 220

Val Phe Asp Pro Gln Glu His Glu Asn Ile Asn Gly Val Pro Pro His
225                 230                 235                 240

Leu Gly His Pro Phe His Trp Gly Gly His Glu Arg Ser Ser Thr Thr
                245                 250                 255

Lys Pro Pro Phe Lys Pro His Gly Ser Arg Asp His His Pro His
            260                 265                 270

Lys Pro His Glu His Gly Pro Pro Pro Asp Glu Arg Asp His
        275                 280                 285

Ser His Gly Pro Pro Leu Pro Gln Gly Pro Pro Leu Leu Pro Met
    290                 295                 300

Ser Cys Ser Ser Cys Gln His Ala Thr Phe Gly Thr Asn Gly Ala Gln
```

-continued

```
                305                 310                 315                 320
Arg His Ser His Asn Asn Asn Ser Ser Asp Leu His Pro His Lys His
                    325                 330                 335
His Ser His Glu Gln His Pro His Gly His His Pro His Ala His His
                340                 345                 350
Pro His Glu His Asp Thr His Arg Gln His Pro His Gly His His Pro
            355                 360                 365
His Gly His His Pro His Gly His His Pro His Gly His His Pro His
        370                 375                 380
Gly His His Pro His Cys
385                 390

<210> SEQ ID NO 9
<211> LENGTH: 151
<212> TYPE: PRT
<213> ORGANISM: Homo sapiens

<400> SEQUENCE: 9

His Leu Gly His Pro Phe His Trp Gly Gly His Glu Arg Ser Ser Thr
  1               5                  10                  15
Thr Lys Pro Pro Phe Lys Pro His Gly Ser Arg Asp His His His Pro
                20                  25                  30
His Lys Pro His Glu His Gly Pro Pro Pro Asp Glu Arg Asp
            35                  40                  45
His Ser His Gly Pro Pro Leu Pro Gln Gly Pro Pro Leu Leu Pro
        50                  55                  60
Met Ser Cys Ser Ser Cys Gln His Ala Thr Phe Gly Thr Asn Gly Ala
 65                  70                  75                  80
Gln Arg His Ser His Asn Asn Asn Ser Ser Asp Leu His Pro His Lys
                 85                  90                  95
His His Ser His Glu Gln His Pro His Gly His His Pro His Ala His
                100                 105                 110
His Pro His Glu His Asp Thr His Arg Gln His Pro His Gly His His
            115                 120                 125
Pro His Gly His His Pro His Gly His His Pro His Gly His His Pro
        130                 135                 140
His Gly His His Pro His Cys
145                 150

<210> SEQ ID NO 10
<211> LENGTH: 25
<212> TYPE: PRT
<213> ORGANISM: Homo sapiens

<400> SEQUENCE: 10

Cys His Asp Phe Gln Asp Tyr Gly Pro Cys Asp Pro Pro His Asn
  1               5                  10                  15
Gln Gly His Cys Cys His Gly His Gly
                20                  25

<210> SEQ ID NO 11
<211> LENGTH: 26
<212> TYPE: PRT
<213> ORGANISM: Homo sapiens

<400> SEQUENCE: 11

Gly Pro Pro Pro Gly His Leu Arg Arg Arg Gly Pro Gly Lys Gly Pro
  1               5                  10                  15
```

```
Arg Pro Phe His Cys Arg Gln Ile Gly Ser
            20                  25
```

<210> SEQ ID NO 12
<211> LENGTH: 36
<212> TYPE: PRT
<213> ORGANISM: Homo sapiens

<400> SEQUENCE: 12

```
Val Tyr Arg Leu Pro Pro Leu Arg Lys Gly Glu Val Leu Pro Leu Pro
 1               5                  10                  15

Glu Ala Asn Phe Pro Ser Phe Pro Leu Pro His His Lys His Pro Leu
            20                  25                  30

Lys Pro Asp Asn
            35
```

<210> SEQ ID NO 13
<211> LENGTH: 32
<212> TYPE: PRT
<213> ORGANISM: Homo sapiens

<400> SEQUENCE: 13

```
Gln Pro Phe Pro Gln Ser Val Ser Glu Ser Cys Pro Gly Lys Phe Lys
 1               5                  10                  15

Ser Gly Phe Pro Gln Val Ser Met Phe Phe Thr His Thr Phe Pro Lys
            20                  25                  30
```

<210> SEQ ID NO 14
<211> LENGTH: 525
<212> TYPE: PRT
<213> ORGANISM: Homo sapiens

<400> SEQUENCE: 14

```
Met Lys Ala Leu Ile Ala Ala Leu Leu Ile Thr Leu Gln Tyr Ser
 1               5                  10                  15

Cys Ala Val Ser Pro Thr Asp Cys Ser Ala Val Glu Pro Glu Ala Glu
            20                  25                  30

Lys Ala Leu Asp Leu Ile Asn Lys Arg Arg Arg Asp Gly Tyr Leu Phe
            35                  40                  45

Gln Leu Leu Arg Ile Ala Asp Ala His Leu Asp Arg Val Glu Asn Thr
        50                  55                  60

Thr Val Tyr Tyr Leu Val Leu Asp Val Gln Glu Ser Asp Cys Ser Val
 65                  70                  75                  80

Leu Ser Arg Lys Tyr Trp Asn Asp Cys Glu Pro Pro Asp Ser Arg Arg
                85                  90                  95

Pro Ser Glu Ile Val Ile Gly Gln Cys Lys Val Ile Ala Thr Arg His
            100                 105                 110

Ser His Glu Ser Gln Asp Leu Arg Val Ile Asp Phe Asn Cys Thr Thr
            115                 120                 125

Ser Ser Val Ser Ser Ala Leu Ala Asn Thr Lys Asp Ser Pro Val Leu
        130                 135                 140

Ile Asp Phe Phe Glu Asp Thr Glu Arg Tyr Arg Lys Gln Ala Asn Lys
145                 150                 155                 160

Ala Leu Glu Lys Tyr Lys Glu Glu Asn Asp Phe Ala Ser Phe Arg
                165                 170                 175

Val Asp Arg Ile Glu Arg Val Ala Arg Val Arg Gly Gly Glu Gly Thr
            180                 185                 190
```

```
Gly Tyr Phe Val Asp Phe Ser Val Arg Asn Cys Pro Arg His His Phe
        195                 200                 205

Pro Arg His Pro Asn Val Phe Gly Phe Cys Arg Ala Asp Leu Phe Tyr
    210                 215                 220

Asp Val Glu Ala Leu Asp Leu Glu Ser Pro Lys Asn Leu Val Ile Asn
225                 230                 235                 240

Cys Glu Val Phe Asp Pro Gln Glu His Glu Asn Ile Asn Gly Val Pro
                245                 250                 255

Pro Leu Gly His Pro Phe His Trp Gly His Glu Arg Ser Ser
            260                 265                 270

Thr Thr Lys Pro Pro Phe Lys Pro His Gly Ser Arg Asp His His His
        275                 280                 285

Pro His Lys Pro His Glu His Gly Pro Pro Pro Pro Asp Glu Arg
    290                 295                 300

Asp His Ser His Gly Pro Pro Leu Pro Gln Gly Pro Pro Leu Leu
305                 310                 315                 320

Pro Met Ser Cys Ser Ser Cys Gln His Ala Thr Phe Gly Thr Asn Gly
                325                 330                 335

Ala Gln Arg His Ser His Asn Asn Asn Ser Ser Asp Leu His Pro His
        340                 345                 350

Lys His His Ser His Glu Gln His Pro His Gly His His Pro His Ala
        355                 360                 365

His His Pro His Glu His Asp Thr His Arg Gln His Pro His Gly His
        370                 375                 380

His Pro His Gly His His Pro His Gly His His Pro His Gly His His
385                 390                 395                 400

Pro His Gly His His Pro His Cys His Asp Phe Gln Asp Tyr Gly Pro
        405                 410                 415

Cys Asp Pro Pro Pro His Asn Gln Gly His Cys Cys His Gly His Gly
                420                 425                 430

Pro Pro Pro Gly His Leu Arg Arg Arg Gly Pro Gly Lys Gly Pro Arg
        435                 440                 445

Pro Phe His Cys Arg Gln Ile Gly Ser Val Tyr Arg Leu Pro Pro Leu
        450                 455                 460

Arg Lys Gly Glu Val Leu Pro Leu Pro Glu Ala Asn Phe Pro Ser Phe
465                 470                 475                 480

Pro Leu Pro His His Lys His Pro Leu Lys Pro Asp Asn Gln Pro Phe
                485                 490                 495

Pro Gln Ser Val Ser Glu Ser Cys Pro Gly Lys Phe Lys Ser Gly Phe
            500                 505                 510

Pro Gln Val Ser Met Phe Phe Thr His Thr Phe Pro Lys
            515                 520                 525

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Asp Leu His Pro His Lys His His Ser His Glu Gln His Pro His Gly
  1               5                  10                  15

<210> SEQ ID NO 16
```

```
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Lys His His Ser His Glu Gln His Pro His Gly His His Pro His Ala
 1               5                  10                  15

His His Pro His Glu His Asp Thr His Gly
            20                  25

<210> SEQ ID NO 17
<211> LENGTH: 25
<212> TYPE: PRT
<213> ORGANISM: Homo sapiens

<400> SEQUENCE: 17

Lys His His Ser His Glu Gln His Pro His Gly His His Pro His Ala
 1               5                  10                  15

His His Pro His Glu His Asp Thr His
            20                  25

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala His His Pro His Glu His Asp Thr His Arg Gln His Pro His Gly
 1               5                  10                  15

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Asp Leu His Pro His Glu Gln His Pro His Glu His Asp Thr His Gly
 1               5                  10                  15

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Leu His Pro His Glu Gln His Pro His Glu His Asp Thr His
 1               5                  10                  15

<210> SEQ ID NO 21
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term acetylated
<220> FEATURE:
<223> OTHER INFORMATION: C-term amidated

<400> SEQUENCE: 21

Ala His His Pro His Glu His Asp Thr His Arg Gln His Pro His
1               5                   10                  15

<210> SEQ ID NO 22
<211> LENGTH: 15
<212> TYPE: PRT
<213> ORGANISM: Homo sapiens

<400> SEQUENCE: 22

Ala His His Pro His Glu His Asp Thr His Arg Gln His Pro His
1               5                   10                  15

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<223> OTHER INFORMATION: C-term amidated

<400> SEQUENCE: 23

Ala His His Pro His Glu His Asp Thr His
1               5                   10

<210> SEQ ID NO 24
<211> LENGTH: 10
<212> TYPE: PRT
<213> ORGANISM: Homo sapiens

<400> SEQUENCE: 24

Ala His His Pro His Glu His Asp Thr His
1               5                   10

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<223> OTHER INFORMATION: C-term amidated

<400> SEQUENCE: 25

Ala His His Pro His
1               5

<210> SEQ ID NO 26
<211> LENGTH: 5
<212> TYPE: PRT
<213> ORGANISM: Homo sapiens

<400> SEQUENCE: 26

Ala His His Pro His
1               5
```

```
<210> SEQ ID NO 27
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term acetylated
<220> FEATURE:
<223> OTHER INFORMATION: C-term amidated

<400> SEQUENCE: 27

Glu His Asp Thr His
  1               5

<210> SEQ ID NO 28
<211> LENGTH: 5
<212> TYPE: PRT
<213> ORGANISM: Homo sapiens

<400> SEQUENCE: 28

Glu His Asp Thr His
  1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 29

His His His His His His
  1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      5xHis tag

<400> SEQUENCE: 30

His His His His His
  1               5

<210> SEQ ID NO 31
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Cys Arg His Ser His Asn Asn Asn Ser Ser Asp Leu His Pro His Lys
  1               5                  10                  15

His His Ser His Glu Gln His Pro His
             20                  25
```

ENDOGENOUS PEPTIDE AND ACTIVE SUBFRAGMENTS THEREOF

CROSS-REFERENCE TO RELATED APPLICATIONS

This application is a National Stage application under 35 U.S.C. §371 and claims the benefit under 35 U.S.C. §119(a) of International Application No. PCT/SE2004/001091 having an International Filing Date of Jul. 5, 2004, which claims the benefit of priority of Swedish Application Serial Number 0301988-2 having a filing date of Jul. 7, 2003 and U.S. Provisional Application Ser. No. 60/485,185 having a filing date of Jul. 7, 2003, all of which are incorporated herein in their entirety.

FIELD OF THE INVENTION

The invention relates to the field of angiogenesis, and more particularly to the use of a biologically active substantially pure consecutive polypeptide, comprising a central region of human Histidine-Rich Glycoprotein (HRGP), and subfragments derived from said central region, all characterized by having anti-angiogenic activity. Said central region of human HRGP is by the present inventors shown to comprise an independent endogenous fragment of human HRGP, which naturally occurs in the human body.

In the following, one of the preferred subfragments of said central region of human HRGP will be referred to as Pep2. Furthermore, a presently minimal active entity derived from said Pep2, has been identified. In addition, other, equally preferred subfragments of various lengths derived from the central region of human HRGP are also identified and encompassed by the present invention.

BACKGROUND

Angiogenesis, the formation of new capillaries from already existing blood vessels, is a procedure which is essential during development and during physiological conditions that require increased vascularisation, such as wound healing and the menstrual cycle. The resting vasculature is tightly regulated by a balance between pro- and anti-angiogenic factors. This balance is disturbed in a number of pathological processes, resulting in deficient angiogenesis, as in ischemic conditions, or excessive angiogenesis, as in rheumatoid arthritis, diabetic retinopathy and tumour growth. It has lately become well established that many types of tumours need to stimulate infiltration of new capillaries to grow and metastasise. Many interesting new therapies, based on pro- and anti-angiogenic substances, are therefore currently being tested in the clinic (Risau et al (1997), Carmeliet et al (2000), Folkman et al (1995, 2000), Hanahan et al (2000), Kerbel et al (2000)).

Histidine Rich Glycoprotein (HRGP) was identified by Heimburger et al in 1972. The protein is synthesized in the liver and has an unusually high content of Pro and His residues. These residues are predominantly situated in a His/Pro region in the centre of the protein and seem to be critical for its function. Until recently, though, very little has been known about the physiological role of HRGP. For a review, see Heimburger et al (1972), Koide et al (1986).

HRGP is present in human plasma at a concentration of approximately 100 μg/ml, which is considered to be very high. The amino acid sequence of mouse, rat, rabbit and human HRGP have been resolved and the protein seems to be well conserved among these vertebrate species (Drasin et al (1996), Hulett et al (2000), Borza et al (1996), Koide et al (1986)). See nucleotide and amino acid sequences of human HRGP under Genbank accession number NM000412.

After proteolytical cleavage from its 18 amino acid long signal peptide, mature HRGP can be divided into three main regions: The N-terminal region, the His/Pro region and the C-terminal region, all displaying different properties. Furthermore, the three regions are suggested to be responsible for binding different ligands. The N-terminal region contains two cysteine protease inhibitor (cystatin)-like stretches (FIG. 1A), which allows the classification of HRGP as a member of the cystatin superfamily, together with .alpha.2HS glycoprotein, cystatin and kininogen, whereas the His/Pro region is very rich in proline and histidine residues resulting in e.g. the human form containing 12 more or less conserved tandem repeats of the pentapeptide HHPHG (SEQ ID NO: 32). In plasma, both the His/Pro region and the C-terminal region are disulfide bonded to the cystatin-like stretches in the N-terminal region (Borza et al (1996)).

High molecular weight kininogen (HK) is structurally related to HRGP, possibly through a gene duplication, as the genes for HK and HRGP are located in close proximity on chromosome 3q. HK has been shown to interfere with endothelial cell function via a part of the protein with sequence similarities to the His/Pro-rich region of HRGP (Zhang et al (2000)).

In general, HRGP binds a variety of different ligands, which can be divided into three major groups: ligands belonging to the coagulation/fibrinolysis system (e.g. heparin, plasminogen and fibrinogen), small ligands (e.g. heme and transition metal ions) and cells (e.g. T-cells, monocytes/macrophages) (Lamb-Wharton et al (1993), Olsen H M et al (1996)).

Furthermore, HGRP binds extracellular matrix components, such as thrombospondin-1 (TSP-1) and vitronectin. Due to its binding to TSP-1, HRGP has previously been suggested to be proangiogenic, (Lijnen et al (1985)).

Juarez et al. (2002) reported that the His/Pro-rich domain of rabbit HRGP purified from plasma inhibits endothelial cell proliferation and vascularisation of matrigel plugs. Using recombinant HRGP, the data could even be extended to provide evidence for in vivo effects on tumour vascularisation. In a previous paper, HRGP was suggested also, under certain circumstances, to promote angiogenesis and to attenuate the anti-angiogenic effect of TSP-1 by complex-formation between the two proteins (Simantov et al (2001)). Juarez et al. suggested that this reported effect is dependent on contamination of the HRGP preparation by plasminogen, which could affect angiogenesis and TSP-1 indirectly.

Other examples of suggested functions of HRGP are modulation of fibrinogenesis (Kluszynski et al, 1997), inhibition of insoluble immune complex formation (Gorgani, 1997) and, recently, potentiation of the ingestion of apoptotic cells by macrophages (Gorgani et al (2002).

In WO 02/076486, the inventors for the first time describe the use of HRGP polypeptides, or its central regions, for the inhibition of anglogenesis. The application further shows methods for inhibiting angiogenesis by administering such a polypeptide to a mammal. Further disclosed are pharmaceutical compositions and articles of manufacture comprising HRGP polypeptides, antibodies and receptors that bind to an HRGP polypeptide, polynucleotides, vectors and host cells that encode HRGP polypeptides.

Later on, WO 02/064621 discloses a selection of HRGP polypeptides, or subfragments thereof, more particularly, specific, H/P-rich, repetitive pentapeptides from a histidine/proline-rich domain of HRGP, as defined by the invention, as being anti-angiogenic. The subfragments are described as inhibitors of angiogenesis and are to be used for the treatment of diseases or conditions, in which angiogenesis is pathogenic. The compounds are predicted to have anti-tumour activity and are proposed to be of use in methods for inhibiting the growth of primary tumours or metastases. Also postulated are antibodies specific for the His-Pro rich domain of HRGP, as stimulators of angiogenesis for promoting neovascularisation in pertinent disease states.

However, none of the previous findings correctly specifies the actual active region, nor the minimal functional entity of HRGP, both being for the first time disclosed by the present invention. Firstly, the inventors are able to show that a central region of human HRGP, defined as amino acid region 240-390 (as seen in SEQ.ID.NO: 2) of mature human HRGP, appears to exist as an endogenous, naturally occurring polypeptide in the human body. This is the first identification of a naturally occurring smaller protein subfragment of human HRGP, comprising similar features to the mature protein, such as anti-angiogenic activity. The identification of this subfragment was then followed by further successful attempts aiming to identify a minimal active entity of the protein, which still possesses an anti-angiogenic activity similar to the naturally occurring fragment. These attempts in turn generated a presently minimal active entity comprising five amino acids derived from the central region of human HRGP and a selection of other subfragments of the central region of human HRGP, also comprising anti-angiogenic activity.

Having thus access to one or more minimal functional entities, a substantially shorter peptide, such as the minimal active entity previously mentioned, or any other HRGP polypeptide/subfragment disclosed by the present invention, can be used as a medicament. The advantages of using a shorter subfragment of HRGP are many, e.g. administration of long peptides is often associated with difficulties due to instability. Also, synthesis of longer peptides is often problematic, whereas shorter peptides are more convenient to synthesise. What is more, they are often less toxic due to higher specificity, which in praxis leads to less side effects.

SUMMARY OF THE INVENTION

The present invention relates to a substantially pure, biologically active and consecutive anti-angiogenic polypeptide comprising a central region of human HRGP (SEQ.ID.NO: 2), having an amino acid length of 151 amino acids comprised in amino acid region 240-390 of mature human HRGP. In the present invention, said polypeptide is shown to comprise a naturally occurring endogenous peptide, which presumably is generated from full-length human HRGP by a naturally occurring proteolytical event. Said endogenous peptide is characterized by comprising anti-angiogenic activity.

The present invention also relates to one or more substantially pure biologically active consecutive anti-angiogenic subfragments derived from said central region of human HRGP, all characterised by having anti-angiogenic activity, and thus considered to be biologically active.

In a preferred embodiment of the present invention, such a substantially pure consecutive anti-angiogenic-subfragment of the central region of HRGP (SEQ.ID.NO:2) is comprised in the amino acid region corresponding to sequence number 330-364 (SEQ.ID.NO:1), of the mature human HRGP protein (SEQ.ID.NO:3).

Another, equally preferred embodiment of the present invention, encloses a substantially pure consecutive anti-angiogenic polypeptide comprising the whole central region, corresponding to SEQ.ID.NO:2.

In another embodiment of the present invention, a substantially pure consecutive anti-angiogenic polypeptide comprises a subfragment of the central region, which subfragment corresponds to SEQ.ID.NO:1.

In yet another embodiment of the present invention, a substantially pure consecutive anti-angiogenic polypeptide comprises a subfragment of the central region, which subfragment corresponds to SEQ.ID.NO:18.

Also enclosed in the present invention is a substantially pure consecutive anti-angiogenic polypeptide comprising a subfragment of said central region, which subfragment comprises approximately 25 amino acids, as listed in SEQ.ID.NO.17. Said subfragment may further comprise said 25 consecutive amino acids derived from human HRGP (SEQ.ID.NO:17), plus an optional additional G residue (residue 26) in the C-terminal end (full sequence disclosed in SEQ.ID.NO:16), said G residue providing additional stability to the subfragment.

Furthermore, the present invention also describes a substantially pure consecutive anti-angiogenic polypeptide comprising a subfragment of said central region, which subfragment comprises approximately 15 amino acids, as listed in SEQ.ID.NO.22. Said subfragment may optionally be acetylated and/or amidated in either of/or both of the C- and/or N-terminal ends of the protein, to provide for stability of the subfragment (disclosed in SEQ.ID.NO:21).

An alternative embodiment of the present invention is a substantially pure consecutive anti-angiogenic polypeptide comprising a subfragment of said central region, which subfragment comprises approximately 10 amino acids, as listed in SEQ.ID.NO.24. Said subfragment may optionally be acetylated and/or amidated in either of/or both of the C- and/or N-terminal ends of the protein, to provide for stability of the subfragment (disclosed in SEQ.ID.NO:23).

In yet another embodiment of the present invention, a substantially pure consecutive anti-angiogenic polypeptide comprises a subfragment of said central region, which subfragment comprises approximately 5 amino acids, such as the subfragments listed in SEQ.ID.NO.26 and SEQ.ID.NO:28. Such a subfragment may optionally be acetylated and/or amidated in either/or both of the C- and/or N-terminal ends of the protein, to provide for stability of the subfragments (disclosed in SEQ.ID.NO:25 and SEQ.ID.NO:27, respectively).

In the present application, the inventors show that human HRGP is proteolytically processed. The convincing results lead the inventors to suggest that human HRGP is naturally and cell/tissue/organ specifically proteolytically processed, to render endogenous biologically active subfragments that have different biological functions.

As proven herein for the first time, the central region of human HRGP, comprised in the amino acid region 240-390 of mature human HRGP, thus corresponds to a naturally occurring consecutive subfragment of mature HRGP, comprising an anti-angiogenically active region of HRGP. What is more, when processed further, said central region can be cleaved to render Pep2, a further biologically active subfragment, corresponding to an equally anti-angiogenically active region of HRGP. In addition, Pep2 is in itself a starting point for identifying a subsidiary minimal functional entity of HRGP, which is an inhibitor of angiogenesis.

As presented in the above, subfragments of Pep2 have been identified in the present invention, which comprise anti-angiogenic activity, and which are able to act as minimal functional entities of HRGP. Such a minimal functional entity can e.g. comprise five amino acids derived from Pep2 (e.g. SEQ.ID.NO:15B).

Consequently, the invention features shorter substantially pure consecutive subfragments of the central region of human HRGP, such as Pep10 (SEQ.ID.NO:18), including subfragments of Pep2, which correspond to at least a part of Pep2, characterized by still having anti-angiogenic activity, similar to mature HRGP. Alternatively, the central region of HRGP, or subfragments thereof, such as any of the subfragments disclosed by the present invention, such as Pep2, or a subfragment of Pep2, can of course be extended either N-terminally or C-terminally, to render a longer consecutive subfragment, comprising at least a part of said central region, such as any of the subfragments disclosed by the present invention, such as Pep2, or a subfragment of Pep2, and wherein the longer subfragment still has anti-angiogenic activity.

A substantially pure consecutive anti-angiogenic polypeptide comprising the central region of human histidine rich glycoprotein (HRGP) (SEQ.ID.NO: 2), or a subfragment thereof, such as any of the subfragments disclosed by the present invention, such as Pep2, or a subfragment of Pep2, may be isolated from human HRGP.

In this context, a substantially pure consecutive polypeptide comprising the central region of human histidine rich glycoprotein (HRGP) (SEQ.ID.NO: 2), or a subfragment thereof, such as any of the subfragments disclosed by the present invention, such as Pep2, or a subfragment of Pep2, which is an inhibitor of angiogenesis, can be produced recombinantly, synthetically, or be purified and/or isolated from plasma.

It should be emphasized that in this context, said substantially pure consecutive anti-angiogenic polypeptide comprising the central region of human histidine rich glycoprotein (HRGP) (SEQ.ID.NO: 2), or a subfragment thereof, such as any of the subfragments disclosed by the present invention, such as Pep2, or a subfragment of Pep2, is characterised in that it does not bind to thrombospondin or promote angiogenesis.

Furthermore, said substantially pure consecutive polypeptide comprising the central region of human histidine rich glycoprotein (HRGP) (SEQ.ID.NO: 2), or a subfragment thereof, such as any of the subfragments disclosed by the present invention, such as Pep2, or a subfragment of Pep2, which is an inhibitor of angiogenesis, may in a preferred embodiment of the invention be comprised in a pharmaceutical composition. Said pharmaceutical composition may optionally comprise any or all of the following components: an anti-angiogenic agent, an anti-neoplastic agent, an anti-inflammatory agent and/or an effective amount of zink. Also, the pharmaceutical composition may further comprise a pharmaceutical carrier acceptable for administration to a mammal.

The present invention in one embodiment comprises a substantially pure consecutive anti-angiogenic polypeptide, which polypeptide comprises the central region of human histidine rich glycoprotein (HRGP) (SEQ.ID.NO: 2), or a subfragment of said central region of human HRGP, such as any of the subfragments disclosed by the present invention, such as Pep2 (SEQ.ID.NO:1), or a subfragment of Pep2, or a pharmaceutical composition, as described by the invention, for use as a medicament.

In another embodiment, the present invention relates to the use of said substantially pure consecutive anti-angiogenic polypeptide comprising the central region of human HRGP, or a subfragment thereof, such as any of the subfragments disclosed by the present invention, such as Pep2, or subfragments of Pep2, or a pharmaceutical composition as described by the invention, for the manufacture of a medicament for inhibiting anglogenesis in a mammal.

Typically, said medicament will be employed for treating and/or preventing cancer in a mammal, e.g. for inhibiting tumor growth in a mammal, and/or for treating and/or inhibiting myocardial angiogenesis, diabetic retinopathy, diabetic neovascularization, inappropriate wound healing, or an inflammatory disease in a mammal.

Said mammal in any of the above embodiments may be a mouse, rat or a human.

In yet another embodiment, the present invention relates to a method for inhibiting angiogenesis in a mammal, which method comprises administering a substantially pure consecutive anti-angiogenic polypeptide, such as the central region of human HRGP, or a subfragment thereof, such as any of the subfragments disclosed by the present invention, such as Pep2, or subfragments of Pep2, or a pharmaceutical composition as described by the invention, to a mammal in need thereof.

In a presently preferred embodiment, said substantially pure consecutive anti-angiogenic polypeptide comprising a subfragment of the central region of human HRGP (SEQ.ID.NO:2), corresponds to SEQ.ID.NO:1, or an amino acid sequence which is at least 70% identical to SEQ.ID.NO:1. Alternatively, said subfragment of HRGP, which is an inhibitor of angiogenesis, corresponds to an amino acid being at least 75% homologous to SEQ.ID.NO:1. Also comprised is a subfragment of SEQ.ID.NO: 1, such as any of the subfragments disclosed by the present invention, or an amino acid sequence which is at least 70% identical to said subfragment, which is an inhibitor of angiogenesis and corresponds to an amino acid being at least 75% homologous to said subfragment.

Furthermore a multimer is envisioned, wherein a monomer corresponds to a substantially pure consecutive anti-angiogenic polypeptide comprising the central region of human HRGP, or a subfragment thereof, such as any of the subfragments disclosed by the present invention, such as Pep2, or a subfragment of Pep2, which is an inhibitor of angiogenesis. Said multimer displays anti-angiogenic activity.

Also related to in the present context, is a nucleic acid sequence encoding a substantially pure consecutive anti-angiogenic polypeptide comprising the central region of human histidine rich glycoprotein (HRGP) (SEQ.ID.NO:2), or a subfragment thereof, such as any of the subfragments disclosed by the present invention, such as Pep2, or a subfragment of Pep2, which is an inhibitor of angiogenesis, and a vector comprising said nucleic acid sequence, as well as a host cell including said vector.

Said vector may optionally be operatively linked to a promoter and/or additional regulatory sequences that regulate the expression of said nucleic acid sequence in a eukaryotic or prokaryotic host cell.

Said host cell may be selected from a group comprising mammalian cells, such as human, mouse, or rat cells, and bacteria, yeast or insect cells.

Accordingly, the present invention also comprises a method for inhibiting angiogenesis in a mammal, which method comprises administering an isolated nucleic acid, a host cell, and/or a vector, to a mammal in need thereof.

The invention is described in more detail in the following sections.

DETAILED DESCRIPTION OF THE INVENTION

The present invention comprises an isolated or synthetically produced, substantially pure, consecutive polypeptide, comprising the central region of human Histidine Rich Glycoprotein (HRGP) (SEQ.ID.NO:3), or a subfragment thereof, such as any of the subfragments disclosed by the present invention, such as Pep2, or subfragments of Pep2, which comprise anti-angiogenic activity. Said polypeptide comprising the central region of human HRGP, is shown by the inventors to comprise an endogenous polypeptide, which is proteolytically cleaved off from the mature protein, to generate an independent self-functional protein characterized by similar anti-angiogenic activity to the mature protein.

A substantially pure consecutive anti-angiogenic subfragment of said central region of human HRGP, is in a most preferred embodiment derived from a region corresponding to amino acids 330-364 of mature human HRGP, being referred to as Pep2 (SEQ.ID.NO:1). Said subfragment is characterised by having anti-angiogenic activity, and an amino acid length of between 5 and 35 amino acids.

Equally preferred, said polypeptide may comprise a subfragment of said central region of human HRGP, such as Pep10 (SEQ.ID.NO:18).

Until recently, the physiological function of HRGP has not been very well known. The present inventors were the first to suggest the involvement of HRGP in anti-angiogenesis (WO02/076486), although the details of its activity were still unknown. In the present invention, the inventors show both in vitro and in vivo that HRGP, purified from human plasma, or recombinantly or synthetically produced, is a potent inhibitor of angiogenesis.

As is shown in experiment 4, HRGP-treatment of fibrosarcoma-bearing mice resulted in decreased tumour angiogenesis and a more than 60% reduction in tumour volume compared to control-treated mice. The smaller tumour volume in HRGP-treated animals was not due to increased apoptosis of the tumour cells, in contrast to what has been reported from studies involving other inhibitors of angiogenesis, for instance TSP-1 and angiostatin. Instead, the proportion of proliferating tumour cells was significantly decreased in HRGP-treated animals, indicating a novel mechanism of action compared to other anti-angiogenic compounds. Most likely, the decreased proliferation reflects a limited supply of oxygen and nutrients to the tumour cells by the less extensive vasculature, compared to control-treated animals. (Auerbach et al 1991, Hawighorst et al (2002), O'Reilly et al (1996)).

The plasma concentration of HRGP is relatively high, 100 µg/ml, already before treatment. The dose used in the tumour studies represents a 100% increase in the amount of HRGP in the treated mice every day, which could accumulate and reach substantially higher concentrations than normal. This argument is supported by the fact that the turnover of HRGP appears slow, with a plasma half-life of three days. (Lijnen et al, 1981) It is noteworthy in this context that it has not been possible to see accumulation of HRGP in the tumour tissue (data not shown).

Without desire to limit the present invention, one plausible theory for the necessity of concentrations up to 100 µg/ml HRGP in plasma is that the protein is not active as a whole, but has to be processed into subfragments of which only some are anti-angiogenic. This is also indicated by the results provided by the present invention.

Confirmative to the present finding, HRGP is sensitive to proteolytic cleavage and degradation products of the protein are often present in purified fractions, giving rise to a characteristic pattern of smaller bands, when resolved on polyacrylamide gels (Kluszynski et al (1997)). Also, as is well known in the field of the art, HRGP binds a variety of endogenous substances, one of them being heparin. The separate domains interact with different ligands, probably due to the variety in function between the domains (Drasin et al (1996), Hulett et al (2000), Borza et al (1996), Koide et al (1986), Heimburger et al (1972))

Figure 12:
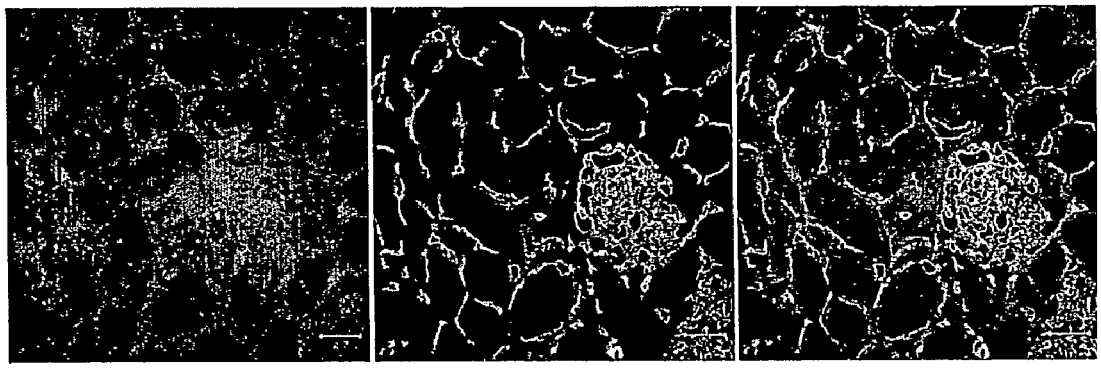

Accordingly, as can be seen in FIG. 12, the present inventors are able to show that the polypeptide comprising the central region of human HRGP, is present in the basement membrane of tumor vessels. Said polypeptide is most likely proteolytically cleaved off the mature protein. Additionally, in experiment 6B, said central region of human HRGP is also shown to inhibit chemotaxis (results shown in FIG. 5A).

As mentioned in a publication by Juarez et al (2002), HRGP has prior been suggested to comprise pro-angiogenic properties due to the binding to Thrombospondin-1 (TSP-1), as it was thought to attenuate the anti-angiogenic properties of TSP-1. In the present application, though, the inventors show, that this is at least not the only function of HRGP. Moreover, presently the separate domains are shown to be responsible for different biological activities, one being anti-angiogenic, another being pro-angiogenic. Besides, the separate domains may be involved in other activities, not involving angiogenesis (Juarez et al (2002), Simantov et al (2001)).

Subsequently, HRGP is herein shown to acquire different properties during certain physiological circumstances. For instance, the heparin-binding affinity of HRGP is modulated and increased in the presence of $Zn^{2+}$ and at low pH, a common environment e.g. in hypoxic tumours. Thus, $Zn^{2+}$ is suggested to be an important cofactor for HRGP, or any subfragment of HRGP, such as any of the subfragments disclosed by the invention, such as Pep2, or subfragments of Pep2, in inhibiting angiogenesis. This is further evidenced by the fact that reduced $Zn^{2+}$-content attenuated HRGP's inhibitory effect on tumour growth (data not shown).

Consequently, it is also clearly conceivable, in line with the results provided by the inventors, that a subfragment of HRGP, such as the central region of human HRGP, or any subfragment of thereof, such as any of the subfragments disclosed by the invention, such as Pep2, or subfragments of Pep2, which is generated in a specific milieu, and which under normal/healthy circumstances is not present in the plasma of the mammal, is responsible for the anti-angiogenic effects observed. This subfragment can e.g. be proteolytically cleaved off from the full-length protein under conditions of increased angiogenesis, e.g. by proteolytic activity produced in and/or secreted from a tumour. Consequently, said anti-angiogenic subfragment can of course also be specifically enriched for during purification of the protein. Such an anti-angiogenic subfragment is demonstrated by the present inventors to comprise the central region of human HRGP, comprised in the amino acid region 240-390 of the mature protein.

In the present application, the central region of HRGP (His/Pro region) (listed as SEQ.ID.NO:2) is demonstrated to be the region responsible for the anti-angiogenic properties of HRGP. As shown in experiment 6B, the isolated central region (His/Pro-rich domain) of human HRGP inhibited chemotaxis as potently as the mature protein. As the corresponding subfragment in rabbit HRGP can be produced by proteolytic processing of full-length HRGP by plasminogen, the inventors presume that this does also apply to human HRGP, since immunoblotting of a purified fraction of full length human HRGP, with an antibody directed against the central region, recognises a subfragment corresponding in size to the recombinantly produced central region. Surprisingly, the truncated version His 4 (as shown in experiment 6B, FIG. 5A) did not inhibit endothelial cell chemotaxis, even though it covers the complete central region. The reason for this is most probably that an improper folding of the protein prevents the active site of the central region from being correctly presented.

Furthermore, a 25 amino acid long subfragment of the central region, located in direct succession to Pep2, and corresponding to amino acids 365-389 of mature human HRGP (SEQ.ID.NO:4) was clearly demonstrated not to be active for inhibiting angiogenesis, as shown in experiment 9. This further strengthens the hypothesis of a minimal functional entity of HRGP, not corresponding to the whole part of the central region, but rather to a shorter fragment such as Pep2, or any subfragments thereof disclosed by the present invention. This is also further shown by the inventors in the experimental section.

Additionally, the inventors are able to show that a smaller subfragment of the central region of human HRGP comprises anti-angiogenic activity in a chemotaxis assay. The results of experiments performed are shown in table 2.

Accordingly, the present inventors could convincingly show that the central region comprises an active part of human HRGP, and that a cell, tissue, or organ specific proteolytic cleavage of the full-length protein during, e.g. angiogenesis, inflammation, or in/or in the vicinity of a tumour, most probably leads to activation of at least one of HRGP's anti-angiogenic properties, either by facilitating the exposure of a previously hidden active site/region of said central region, or by releasing one or more minimum active fragment(s) carrying said same or another active site/region.

The potent inhibitory effect of a substantially pure consecutive anti-angiogenic polypeptide comprising the central region of human HRGP (SEQ.ID.NO: 2), or a subfragment thereof, such as any of the subfragments disclosed by the present invention, such as Pep2, or a subfragment of Pep2, on tumour growth, most likely mediated via decreased tumour angiogenesis, provides an interesting target for further studies. Also, the use of such a polypeptide or subfragment for anti-angiogenesis, as a clinical strategy to treat inflammatory diseases, e.g. rheumatoid arthritis, is attractive in many ways.

Since anti-angiogenic therapy directly targets vasculature engaged in active angiogenesis, the risk of unwanted side effects is low, which is even lowered by eliminating the potential side effects of a longer peptide, including e.g. pro-angiogenetic properties. Also, problems with general toxicity are minimized when using therapies based on naturally occurring small proteins. Finally, making use of a body's own response to a specific trait of e.g. tumour cells, namely the naturally expressed and/or secreted proteases that in a sick mammal proteolytically process HRGP to said active subfragments, in itself guarantees an approach to treating a disease that will be less toxic and less hampered by undesired side effects, because the therapy mimics and enhances the hosts natural defense instead of introducing a foreign factor.

Consequently, a substantially pure consecutive anti-angiogenic polypeptide comprising the central region of human histidine rich glycoprotein (HRGP) (SEQ.ID.NO: 2), or a subfragment thereof, such as any of the subfragments disclosed by the present invention, such as Pep2, or a subfragment of Pep2, is a much-preferred peptide for use as a medicament in angiogenesis-dependent disease states, as it is less likely to be toxic and less likely to induce side effects due to higher specificity.

The present inventors successfully demonstrate the anti-angiogenic activity of Pep2 in an animal model, as shown in experiment 10, followed by a dose-response study confirming the in vitro results pointing towards a saturation effect of said Pep2, shown in experiment number 8, thus suggesting a preferable dose for administration.

As previously mentioned, the inventors are also able to show an anti-angiogenic effect of smaller subfragments of the central region of human HRGP, such as a amino acid subfragment comprising only five amino acids (shown in table 2).

In the present context, the term "HRGP" refers to the mature human HRGP peptide, which comprises about 507 amino acid residues and which corresponds to SEQ.ID.NO:3. The mature human HRGP is comprised in the 525 amino acid-long full-length HRGP, as listed in SEQ.ID.NO:14 (see also NM000412) and includes an 18 amino acid-long signal peptide, which is cleaved of in the mature peptide.

A "subfragment", refers to a subfragment of variable size, which is typically derived from the central region of human histidine rich glycoprotein (HRGP) (SEQ.ID.NO: 2), such as any of the subfragments disclosed by the invention, such as Pep2, or a subfragment of Pep2, which comprises angiogenic properties and which is an inhibitor of angiogenesis.

"Pep2" refers to an amino acid subfragment of 35 amino acids (SEQ.ID.NO:1), which is derived from the central region (SEQ.ID.NO:2) of human HRGP, and which corresponds to SEQ.ID.NO:1.

"Pep3" refers to an amino acid subfragment of 25 amino acid residues corresponding SEQ.ID.NO:4, which is derived from the central region of HRGP and has further been described in WO02/064621.

A "His-Peptide" is an amino acid fragment, comprising approximately 25 histidine residues, which in one embodiment corresponds to SEQ.ID.NO:5. Further, "His2" corresponds to SEQ.ID.NO:6, "His3" corresponds to SEQ.ID.NO: 7, "His4" to SEQ.ID.NO:8, and finally, "His5" to SEQ: ID.NO:9. The results displaying the ability of inducing chemotaxis of these truncated versions of HRGP are shown and further discussed in experiment number 7.

Additionally, comprised in SEQ.ID.NO:10-13 are Pep4-Pep7, which are all shown in FIG. 5A. These peptides are all derived from an amino acid region outside of the central region of human HRGP.

"Pep8", refers to an amino acid sequence derived from the central region of human HRGP, which is disclosed in SEQ.ID.NO: 15. Pep8 comprises 16 amino acids. Pep8 was proven not to be effective in a chemotaxis assay (table 2).

"Pep9 A&B" refers to an amino acid sequence derived from the central region of human HRGP, which is disclosed in SEQ.ID.NO:16 and 17. Said sequence may optionally be modified in the C-terminal end with an additional Glycine (G) amino acid residue (SEQ.ID.NO:16), to provide stability to the polypeptide. The pure human HRGP sequence is also related to in the present invention, and is disclosed in SEQ.ID.NO:17. The modified sequence comprises 26 amino acids. The non-modified sequence comprises 25 amino acids.

"Pep10" refers to an amino acid sequence derived from the central region of human HRGP, which is disclosed in SEQ.ID.NO:18. Pep10 comprises 16 amino acids.

"Pep11 A&B" refers to a non-consecutive amino acid sequence derived from the central region of human HRGP, which is disclosed in SEQ.ID.NO:19 and 20. Said sequence may optionally be modified in the C-terminal end with an additional Glycine (G) amino acid residue (SEQ.ID.NO:20). Said sequence was proven not to be effective in a chemotaxis assay (table 2).

"Pep12 A&B" refers to an amino acid sequence derived from the central region of human HRGP, which is disclosed in SEQ.ID.NO:21 and 22. Said sequence may optionally be modified in either or both of the C-terminal and/or N-terminal ends, with an acetylation and/or an amidation modification, respectively, to provide stability to the polypeptide. The modified sequence is disclosed in SEQ.ID.NO:21. The pure human HRGP sequence is disclosed in SEQ.ID.NO:22. Both the modified and the non-modified sequences are hereby enscoped by the present invention.

"Pep13 A&B" refers to an amino acid sequence derived from the central region of human HRGP, which is disclosed in SEQ.ID.NO:23 and 24. Said sequence may optionally be modified in either or both of the C-terminal and/or N-terminal ends, with an acetylation and/or an amidation, respectively, to provide stability to the polypeptide. The modified sequence is disclosed in SEQ.ID.NO:23. The pure human HRGP sequence is disclosed in SEQ.ID.NO:24. Both the modified and the non-modified sequence are hereby enscoped by the present invention.

"Pep14 A&B" refers to an amino acid sequence derived from the central region of human HRGP, which is disclosed in SEQ.ID.NO:25 and 26. Said sequence may optionally be modified in either or both of the C-terminal and/or N-terminal ends, with an acetylation and/or an amidation, respectively, to provide stability to the polypeptide. The modified sequence is disclosed in SEQ.ID.NO:25. The pure human HRGP sequence is disclosed in SEQ.ID.NO:26. Both the modified and the non-modified sequence are hereby enscoped by the present invention.

"Pep15 A&B" refers to an amino acid sequence derived from the central region of human HRGP, which is disclosed in SEQ.ID.NO:27 and 28. Said sequence may optionally be modified in either or both of the C-terminal and/or N-terminal ends, with an acetylation and/or an amidation, respectively, to provide stability to the polypeptide. The modified sequence is disclosed in SEQ.ID.NO:27. The pure human HRGP sequence is disclosed in SEQ.ID.NO:28. Both the modified and the non-modified sequence are hereby enscoped by the present invention.

In a general aspect of the present invention, a consecutive subfragment of the central region of human histidine rich glycoprotein (HRGP) (SEQ.ID.NO: 2), characterised in having anti-angiogenic activity, is preferably selected from a 25 to 151 amino acid residues long peptide, such as from an 25, 30, 35, 40, 45, 50, 55, 60, 65, 70, 75, 80, 85, 90, 95, 100, 105, 110, 115, 120, 125, 130, 135, 140, 145, 146, 147, 148, 149, 150 or an 151 amino acid residues long peptide. It should however be understood that such a peptide comprising a consecutive subfragment of the central region, may comprise any amount of amino acids residues between 25 and 151. Such a consecutive subfragment does not correspond to Pep3 (SEQ.ID.NO:4), or to subfragments derived from Pep3 which are 5 amino acids or longer.

In another embodiment of the present invention, a consecutive subfragment of the central region of human histidine rich glycoprotein (HRGP) (SEQ.ID.NO: 2), characterised in having anti-angiogenic activity, is preferably selected from a 3 to 25 amino acid residues long peptide, such as from 3, 4, 5, 6, 7, 8, 9, 10, 11, 12, 13, 14, 15, 16, 17, 18, 19, 20 or 25 amino acid residues. It should however be understood that such a peptide, comprising a consecutive subfragment of the central region, may comprise any amount of amino acids between 3 and 25. Such a consecutive subfragment does not correspond to Pep3 (SEQ.ID.NO:4), or to subfragments derived from Pep3 which are 5 amino acids or longer. In another aspect of the invention, said peptide comprising a consecutive subfragment of the central region, may also comprise less than 3 amino acids.

In a presently most preferred embodiment, a substantially pure consecutive subfragment of the central region of human histidine rich glycoprotein (HRGP) (SEQ.ID.NO: 2), comprises a subfragment comprising amino acid region 330-364 of mature human HRGP (SEQ.ID.NO:1), or a subfragment derived from said region. Said subfragments are characterised in having anti-angiogenic activity and an amino acid length of between 3 and 35 amino acids, such as between 3 and 5, 3 and 8, 3 and 10, 3 and 15, 3 and 20, 3 and 25, 10 and 25, 10 and 30, 20 and 35, or between 25 and 35 amino acids. Such a subfragment may comprise 3, 4, 5, 6, 7, 8, 9, 10, 11, 12, 13, 14, 15, 16, 17, 18, 19, 20, 21, 22, 23, 24, 25, 26, 27, 28, 29, 30, or 35 consecutive amino acids. It should however be understood that such a peptide, comprising a consecutive subfragment of the central region, may comprise any amount of amino acids between 3 and 35 amino acids. In another aspect of the invention, said peptide comprising a consecutive subfragment of the central region, may also comprise less than 3 amino acids.

Other typical embodiments of the invention, are peptides or subfragments of a peptide corresponding to one of the amino acid sequences as listed in the accompanying sequence listing as SEQ.ID.NO. 10-13 (Pep4-Pep7).

Other presently preferred embodiments of the invention are peptides or fragments listed in SEQ.ID.NO:16-18 or 21-28.

A consecutive amino acid fragment, in the present context, relates to a sequence of amino acids, which is derived successively and uninterrupted from the original amino acid sequence, to which it correlates. In particular, Pep2 thus corresponds to a naturally occurring succession of amino acids of the central region of human histidine rich glycoprotein (HRGP) (SEQ.ID.NO: 2), namely to amino acids 330-364 of full length human HRGP, as listed in amino acid sequence SEQ.ID.NO.1.

Additionally, any conservative variant of the sequence of a substantially pure consecutive subfragment of the central region of human histidine rich glycoprotein (HRGP) (SEQ.ID.NO: 2), characterised in having anti-angiogenic activity, such as any of the subfragments disclosed by the present invention, such as Pep2, or a subfragment of Pep2, which is an inhibitor of angiogenesis, is by virtue of its functional relationship to said subfragment considered to be inside the scope of the present invention.

A conservative variant of a sequence is in the present context defined as an amino acid sequence which is conserved at least 70%, such as 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, when comparing variants of the same amino acid sequence between different species. The degree of conservation of a variant can, as is well known in the field, be calculated according to its derivation of PAM (see Dayhoff, Schwartz, and Orcutt (1978)), or based on comparisons of Blocks of sequences derived from the Blocks database as described by Henikoff and Henikoff (1992).

Conservative substitutions may be made, for example according to table 1 below. Amino acids in the same block in the second column and preferably in the same line in the third column may be substituted for each other:

TABLE 1

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

Such replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, L-α-amino butyric acid*, L-g-amino butyric acid*, L-a-amino isobutyric acid*, L-e-amino caproic acid#, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid # and L-Phe (4-benzyl)*. The notation * is herein utilised to indicate the hydrophobic nature of the derivative whereas # is utilised to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or b-alanine residues. A further form of variation, involves the presence of one or more amino acid residues in peptoid form, which will be well understood by those skilled in the art. For the avoidance of doubt, "the peptoid form" is used to refer to variant amino acid residues wherein the a-carbon substituent group is on the residue's nitrogen atom rather than the α-carbon. Processes for preparing peptides in the peptoid form are known in the art, see for example, Simon R J et al, (1992) and Horwell D C et al (1995).

Polypeptides and/or subfragments of the invention may be in a substantially isolated form. It will be understood that the polypeptide/amino acid sequence may be mixed with carriers or diluents, which will not interfere with the intended purpose of the peptide/amino acid sequence and still be regarded as substantially isolated.

The term "substantially pure" is in the present context employed to describe a polypeptide/amino acid sequence of the invention in its substantially purified form, in which case it will generally comprise the peptide/amino acid sequence or a fragment thereof, in a preparation in which more than 90%, e.g. 95%, 98% or 99% of the protein in the preparation is a peptide of the invention.

Furthermore, any amino acid sequence being at least 70% identical, such as being at least 72%, 75%, 77%, 80%, 82%, 85%, 87%, 90%, 91%, 92%, 93%, 94%, 95%, 96%, 97%, 98%, or 99% identical with the amino acid sequence of a substantially pure consecutive polypeptide comprising the central region of human histidine rich glycoprotein (HRGP) (SEQ.ID.NO: 2), or a subfragment thereof, such as any of the subfragments disclosed by the invention, such as Pep2, or a subfragment thereof, characterised in having anti-angiogenic activity, is also considered to be inside the scope of the present invention.

By a polypeptide having an amino acid sequence at least, for example 95% identical to a reference amino acid sequence, is intended that the amino acid sequence of the polypeptide is identical to the reference sequence except that the amino acid sequence may include up to 5 point mutations per each 100 amino acids of the reference amino acid sequence. In other words, to obtain a polypeptide having an amino acid sequence at least 95% identical to a reference amino acid sequence: up to 5% of the amino acids in the reference sequence may be deleted or substituted with another amino acid, or a number of amino acids up to 5% of the total amino acids in the reference sequence may be inserted into the reference sequence. These mutations of the reference sequence may occur at the amino or carboxy terminal positions of the reference amino acid sequence or anywhere between those terminal positions, interspersed either individually among amino acids in the reference sequence or in one or more contiguous groups within the reference sequence.

In the present invention, a local algorithm program is best suited to determine identity. Local algorithm programs, such as (Smith-Waterman) compare a subsequence in one sequence with a subsequence in a second sequence, and find the combination of subsequences and the alignment of those subsequences, which yields the highest overall similarity score. Internal gaps, if allowed, are penalized. Local algorithms work well for comparing two multidomain proteins, which have a single domain, or just a binding site in common.

Methods to determine identity and similarity are codified in publicly available programs. Preferred computer program methods to determine identity and similarity between two sequences include, but are not limited to, the GCG program package (Devereux, J et al (1994)) BLASTP, BLASTN, and FASTA (Altschul, S. F. et al (1990)). The BLASTX program is publicly available from NCBI and other sources (BLAST Manual, Altschul, S. F. et al, Altschul, S. F. et al (1990)). Each sequence analysis program has a default scoring matrix and default gap penalties. In general, a molecular biologist would be expected to use the default settings established by the software program used.

The advantages of using a smaller subfragment of HRGP, such as any of the subfragments disclosed by the present invention, such as Pep2, or a subfragment derived therefrom, for the treatment of angiogenesis-related diseases are obvious to the person skilled in the art. For example, smaller peptide subfragments are more convenient for the development of a pharmaceutical. Longer peptides are considered difficult to handle, as they are often unstable and readily degraded once distributed in the body. Further, a shorter peptide is also considered to have fewer side effects, as the likelihood of the shorter peptide to interact with other biologically active substances is lesser than for a longer peptide.

As used herein, a "pro-angiogenic activity" or "pro-angiogenic property" is defined as an activity, which promotes angiogenesis. An amino acid sequence with pro-angiogenic activity promotes angiogenesis by interaction with other factors involved in the process leading to angiogenesis, or by direct action in specific subprocesses during angiogenesis such as, but not limited to, chemotaxis. Furthermore, the pro-angiogenic activity is characterized in that it will promote angiogenesis in naturally occurring physiological processes such as embryonic growth, wound healing, and in pathological processes such as rheumatoid arthritis, systemic lupus erythematosus, arteriosclerosis and cancer. Examples of pro-angiogenic factors are fibroblast growth factors, Follistatin, G-CSF, IL-8, TGF-α, TGF-β etc As used herein, an amino acid sequence/peptide, which displays an "anti-angiogenic activity" or "anti-angiogenic property" is defined as displaying an activity, which inhibits angiogenesis. The anti-angiogenic amino acid sequence/peptide inhibits angiogenesis by interaction with other factors involved in the process leading to angiogenesis or by direct action in specific subprocesses during angiogenesis such as, bit not limited to, chemotaxis. Furthermore, the anti-angiogenic activity is characterised in that it will inhibit and decrease angiogenesis in naturally occurring physiological processes such as embryonic growth, wound healing, and in pathological processes such as rheumatoid arthritis, systemic lupus erythematosus, arteriosclerosis and cancer. Examples of anti-angiogenic factors are Angiostatin, Angioarrestin, Endostatin, Fibronectin subfragment, Cartilage-derived inhibitor etc As described in the present invention, HRGP polypeptides/ subfragments, such as any of the subfragments disclosed by the present invention, such as Pep2 and subfragments derived therefrom, are in their natural environment produced by a "naturally occurring proteolytical event", characterised in that the polypeptide is cleaved by endogenous enzymes (e.g. proteases) to generate subfragments of which some display biological activity such as being involved in the angiogenesis process. In one embodiment of the present invention, a subfragment may comprise anti-angiogenic properties; in another embodiment a subfragments may comprise pro-angiogenic properties. Furthermore, other subfragments may comprise properties, which do not affect the process of angiogenesis.

Accordingly, as previously described, the naturally occurring polypeptides/subfragments of human HRGP, are suggested to comprise different physiological functions. E.g. in a previous publication, it has been suggested that HRGP interacts with Thrombospondin-1 (TSP-1). In the same publication, it is further suggested that the interaction between TSP-1 and HRGP attenuates the anti-angiogenic properties of TSP-1, thereby proposing a pro-angiogenic role of HRGP. (Juarez et al (2002)). Contrary to this, the present invention, presents convincing results, which support the importance of HRGP as an angiogenesis inhibitor. These contradictory results strengthen the hypothesis that the different subfragments/ polypeptides of HRGP comprise different physiological properties. It is in the present invention further shown that HRGP in its natural environment most frequently occurs as a subfragmented protein. Thus, it is suggested that some of the subfragments derived from HRGP, preferably derived from the central region of the protein, and preferably again, derived from Pep2, comprise the anti-angiogenic activity of HRGP, which is silenced in the unprocessed mature peptide.

A "biologically active subfragment" in the present context, refers to a subfragment, which is active in its biological environment, which is characterised by that it maintains its biological activity when removed from its natural environment. A biologically active subfragment is further characterised in that it is not dependent upon any other stimulants or cofactors to function, but is active in it self. However, it should be mentioned, that a biologically active fragment of HRGP might behave differently depending on the physiological environment such as the presence of $Zn^{2+}$ and a specific pH.

Another aspect of the present invention includes isolated polynucleotide sequences encoding a substantially pure consecutive polypeptide comprising the central region of human histidine rich glycoprotein (HRGP) (SEQ.ID.NO: 2), or subfragments thereof, such as any of the subfragments disclosed by the present invention, such as Pep2, or subfragments derived therefrom, characterised in having anti-angiogenic activity. Such polynucleotides include, but are not limited to, mRNAs, cDNAs and genomic DNAs, as well as diagnostically or therapeutically useful fragments thereof. Also included are variants of such polynucleotides, which variants encode for a fragment, derivative or analogue of a substantially pure consecutive polypeptide comprising the central region of human histidine rich glycoprotein (HRGP) (SEQ.ID.NO: 2), or a subfragment thereof, such as any of the subfragments disclosed by the present invention, such as Pep2, or a subfragment of Pep2, characterised in having anti-angiogenic activity.

Isolated nucleic acid molecules of the invention can be produced by standard techniques. As used herein, "isolated" refers to a sequence corresponding to part or all of a gene encoding an HRGP polypeptide, but free of sequences that normally flank one or both sides of the wild-type gene in a naturally occurring genome. The term "isolated" as used herein with respect to nucleic acids also includes any non-naturally-occurring nucleic acid sequence since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a cDNA or genomic DNA fragment produced by PCR or restriction endonuclease treatment) independent of other sequences as well as recombinant DNA that is incorporated into a vector, an autonomously replicating plasmid, a virus (e.g., a retrovirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Isolated nucleic acids within the scope of the invention can be obtained using any method including, without limitation, common molecular cloning and chemical nucleic acid synthesis techniques. For example, PCR techniques can be used to obtain an isolated nucleic acid containing a nucleic acid sequence sharing identity with art known sequences of HRGP.

PCR refers to a procedure or technique in which target nucleic acids are amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. General PCR techniques are described, for example in "PCR Primer: A Laboratory Manual," Dieffenbach et al (1995). When using RNA as a source of template, reverse transcriptase can be used to synthesize complimentary DNA (cDNA) strands.

Isolated nucleic acids of the invention also can be chemically synthesized, either as a single nucleic acid molecule or as a series of oligonucleotides. For example, one or more pairs of long oligonucleotides (e.g., >100 nucleotides) can be synthesised that contain the desired sequence, with each pair containing a short segment of complementary (e.g., about 15 nucleotides) such that a duplex is formed when the oligonucleotide pair is annealed. DNA polymerase is used to extend the oligonucleotides, resulting in a double-stranded nucleic acid molecule per oligonucleotide pair, which then can be ligated into a vector.

Isolated nucleic acids of the invention also can be obtained by mutagenesis. For example, an isolated nucleic acid that shares identity with an in the art known HRGP sequence can be mutated using common molecular cloning techniques (e.g., site-directed mutagenesis). Possible mutations include, without limitation, deletions, insertions, and substitutions, as well as combinations of deletions, insertions, and substitutions.

In addition, nucleic acid and amino acid databases (e.g., GenBank®) can be used to obtain an isolated polynucleotide within the scope of the invention. For example, a sequence having homology to a nucleic acid sequence encoding an in the art known HRGP subfragment or an amino acid sequence having homology to an in the art known HRGP subfragment amino acid sequence can be used as a query to search GenBank®. Examples of nucleic acids encoding known HRGP polypeptides include the following GenBank® Accession Nos.: NM 000412 (human); AF194028 (mouse); AF 194029 (rat); and U32189 (rabbit).

Furthermore, nucleic acid hybridisation techniques can be used to obtain an isolated nucleic acid within the scope of the invention. Briefly, a nucleic acid sequence encoding a HRGP polypeptide/subfragment can be used as a probe to identify a similar nucleic acid by hybridisation under conditions of moderate to high stringency. Moderately stringent hybridisation conditions include hybridisation at about 42° C. in a hybridisation solution containing 25 mM $KPO_4$ (pH 7.4)@ 5×SSC, 5× Denhart's solution, 50 µg/mL denatured, sonicated salmon sperm DNA, 50% formamide, 10% Dextran sulfate, and 1-15 ng/mL probe (about $5×10^7$ cpm/µg), and wash steps at about 50° C. with a wash solution containing 2×SSC and 0.1% SDS. For high stringency, the same hybridisation conditions can be used, but washes are performed at about 65° C. with a wash solution containing 0.2×SSC and 0.1% SDS.

Once a nucleic acid is identified, the nucleic acid then can be purified, sequenced, and analysed to determine whether it is within the scope of the invention as described herein.

Hybridisation can be done by Southern or Northern analysis to identify a DNA or RNA sequences, respectively that hybridises to a probe. The probe can be labelled with biotin, digoxygenin, an enzyme, or a radioisotope such as $^{32}P$ or $^{35}S$. The DNA or RNA to be analysed can be electrophoretically separated on an agarose or polyacrylamide gel, transferred to nitrocellulose, nylon, or other suitable membrane, and hybridised with the probe using standard techniques well known in the art. See, for example, sections 7.39-7.52 of Sambrook et al (1989).

The present invention also includes vectors comprising isolated polynucleotides encoding the central region of human HRGP, or subfragments thereof, such as any of the subfragments disclosed by the present application, such as Pep2, or subfragments derived therefrom, and host cells comprising these vectors. The vectors of the present invention may include, for example, plasmids, recombinant viruses, cloning vectors, or expression vectors. Host cells may be genetically engineered (transduced or transformed or transfected) with the vectors of this invention. The engineered host cells can be selected from a broad variety such as from plant cells, or eukaryotic cells, such as mammal, insect or yeast cells, or prokaryotic cells, such as bacterial cells. Said host cells can be cultured in conventional nutrient media modified as appropriate for activating promoters, selecting transformants or amplifying the 25 genes of the present invention. The culture conditions, such as temperature, pH and the like, are those previously used with the host cell selected for expression, and will be apparent to the ordinarily skilled artisan.

The term "expression vector" or "expression cassette" as used herein refers to a nucleotide sequence which is capable of affecting expression of a protein coding sequence in a host compatible with such sequences. Expression cassettes include at least a promoter operably linked with the polypeptide coding sequence; and, optionally, with other sequences, e.g., transcription termination signals. Additional factors necessary or helpful in effecting expression may also be included, e.g., enhancers.

"Operably linked" means that the coding sequence is linked to a regulatory sequence in a manner that allows expression of the coding sequence. Known regulatory sequences are selected to direct expression of the desired protein in an appropriate host cell. Accordingly, the term "regulatory sequence" includes promoters, enhancers and other expression control elements. Such regulatory sequences are described in, for example, Goeddel, (1990).

Thus, expression cassettes include plasmids, recombinant viruses, any form of a recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous selfreplicating circular or linear DNA or RNA, e.g., plasmids, viruses, and the like (U.S. Pat. No. 5,217,879), A wide variety of methods are known to the person skilled in the art which can be used to obtain a substantially pure polypeptide/subfragment of HRGP, as previously described. For example, intact or subfragmented HRGP can be purified from freshly collected human plasma by chromatography on phosphocellulose in the presence of proteinase inhibitors following the procedures Kluszynski et al (1997), Rylatt et al (1981)

As shown in experiment 2, the resultant protein is approximately 99% pure, as estimated by SDS-Polyacrylamide Gel Electrophoresis (SDS-PAGE). Many materials can be used as a source to obtain a substantially pure polypeptide, for example tissue culture cells expressing the particular polypeptide of interest can be used to obtain a substantially pure polypeptide. Furthermore, in addition to polypeptide purification techniques such as affinity chromatography and HPLC, other polypeptide synthesis techniques can of course be used to produce the sought after polypeptide.

A substantially pure polypeptide comprising the central region of human HRGP, or subfragments derived therefrom, such as any of the subfragments disclosed by the present invention, such as Pep2, or subfragments derived therefrom, may also be produced by recombinant methods. The cDNA sequences of rabbit (Borza et al. (1996)), rat, mouse (Hulett et al. (2000)) and human (Koide et al. (1986)) HRGP are art known. Methods for the expression of a protein product from a cDNA clone are well known. See, for example, Maniatis et al. (1989). A HRGP polypeptide/subfragment, which is produced, can be any of the polypeptides/subfragments disclosed by the present invention, such as Pep2, or any other subfragments. Suitable expression systems include, without limitation, microorganisms such as bacteria (for example, E. coli and B. subtilis) transformed with recombinant bacteriophage DNA, plasmid DNA, or cosmid DNA expression vectors; yeast (for example, Saccharomyces and Pichia) transformed with recombinant yeast expression vectors; insect cell systems infected with recombinant virus expression vectors (for example, baculovirus); plant cell systems infected with recombinant virus expression vectors (for example, cauliflower mosaic virus (CaMV) and tobacco mosaic virus (TMV)) or transformed with recombinant plasmid expression vectors (for example, Ti plasmid) containing fusion protein nucleotide sequences; or mammalian cell systems (for example, HEK, COS, CHO, BHK, 293, VERO, HeLa, MDCK, W138, and NIH 3T3 cells) transformed with expression constructs containing promoters derived from the genome of mammalian cells (for example, the metallothionein promoter) or from mammalian viruses (for example, the adenovirus late promoter and the vaccinia virus 7.5K promoter). Also useful as host cells are primary or secondary cells obtained directly from a mammal, transfected with a plasmid vector or infected with a viral vector such as herpes viruses, retroviruses, vaccinia viruses, attenuated vaccinia viruses, canary pox viruses, adenoviruses, adeno-associated viruses, lentiviruses and herpes viruses, among others.

Furthermore, synthetic production of HRGP polypeptides/subfragments, is defined as an event were amino acids are attached together to generate a polypeptide/protein during a chemical procedure. This may be performed according to standard protein synthesis procedures.

For diagnostic applications, a substantially pure consecutive polypeptide comprising the central region of human histidine rich glycoprotein (HRGP) (SEQ.ID.NO: 2), or a subfragment thereof, such as any of the subfragments disclosed by the present invention, such as Pep2, or a subfragment derived therefrom, characterised in having anti-angiogenic activity, may be labelled with a detectable moiety. This detectable moiety is capable of producing, either directly or indirectly, a detectable signal. For example, the detectable moiety may be a radioisotope, such as $H^3$, $C^{14}$, $P^{32}$, $s^{35}$, or $I^{125}$; a fluorescent or chemiluminescent compound, such as fluorescein isothiocyanate, rhodamine, or luciferin; or an enzyme, such as alkaline phosphatase, betagalactosidase or horseradish peroxidase. Any method known in the art for conjugating a polypeptide to a detectable moiety may be employed. See, for example, Hunter et al. (1962); David et al. (1974); Pain et al. (1981); and Nygren et al. (1982).

A substantially pure consecutive polypeptide comprising the central region of human HRGP, or a subfragment thereof, such as any of the subfragments disclosed by the present invention, such as Pep2, or a subfragment of Pep2, characterised in having anti-angiogenic activity, may also be coupled to a detectable moiety useful for in vivo imaging to image areas of neovascularisation. The HRGP polypeptide/subfragment may be labelled with a detectable moiety such as a radio-opaque agent or radioisotope and administered to a host, preferably into the bloodstream, and the presence and location of the labelled HRGP polypeptide/subfragment is assayed. The HRGP polypeptide/subfragment may be labelled with any moiety that is detectable in a host, whether by nuclear magnetic resonance, radiology, or other detection means known in the art. Radioisotope can be, for example, $^{186}Re$, $^{188}Re$, $^{64}Cu$, $^{67}Cu$, $^{212}Bi$, $^{123}I$, $^{131}I$, $^{211}At$, $^{177}Lu$, $^{47}SC$, $^{105}Rh$, $^{109}Pd$, $^{153}Sm$, $^{199}Au$, $^{99m}Tc$, $^{111}In$, $^{124}I$, $^{18}F$, $^{11}C$, $^{198}AU$, $^{75}Br$, $^{76}Br$, $^{77}Br$, $^{13}N$, $^{34m}CI$, $^{38}CI$, $^{52m}Mn$, $^{55}Co$, $^{62}Cu$, $^{68}Ga$, $^{72}As$, $^{76}As$, $^{72}Se$, $^{73}Se$, or $^{71}Se$.

A substantially pure consecutive polypeptide comprising the central region of human histidine rich glycoprotein (HRGP) (SEQ.ID.NO: 2), or a subfragment thereof, such as any of the subfragments disclosed by the present invention such as Pep2, or a subfragment of Pep2, characterised in having anti-angiogenic activity, coupled to a toxin, may be used as a therapeutic agent to target a receptor. Such a polypeptide/subfragment, may be coupled to any toxic polypeptide that mediates a cytotoxic effect within the cytoplasm of a cell by procedures well known in the art. Preferred toxic polypeptides include ribosome inactivating proteins, e.g., plant toxins such as an A chain toxin (e.g., ricin A chain), saporin, bryodin, gelonin, abrin, or pokeweed antiviral protein (PAP), fungal toxins such as α-sarcin, aspergillin, or restrictocin, bacterial toxins such as diphtheria toxin (DT) or *Pseudomonas* exotoxin A, or a ribonuclease such as placental ribonuclease or anglogenin. Other useful toxic polypeptides are the pro-apoptotic polypeptides, e.g., Bax, Bad, Bak, Bim, Bik, Bok, or Hrk. Furthermore, more than one functional fragment (e.g. 2, 3, 4, 6, 8, 10, 15, or 20) of one or more (e.g., 2, 3, 4, or 6) toxins can be coupled to a polypeptide/subfragment of HRGP. Where repeats are included, they can be immediately adjacent to each other, separated by one or more targeting fragments, or separated by a linker peptide as described above. The invention also includes functional fragments of any of these polypeptides coupled to a HRGP polypeptide/subfragment.

The present invention furthermore discloses antibodies comprising specific binding affinity for a substantially pure consecutive polypeptide comprising the central region of human histidine rich glycoprotein (HRGP) (SEQ.ID.NO: 2), or a subfragment thereof, such as any of the subfragments disclosed by the present invention, such as Pep2, or a subfragment derived therefrom, characterised in having anti-angiogenic activity. Antibodies having specific binding affinity for such a polypeptide/subfragment, can be produced through standard methods. As used herein, the terms "antibody" or "antibodies" include intact molecules as well as fragments thereof that are capable of binding to an epitopic determinant in such a HRGP polypeptide or a subfragment thereof. The term "epitope" refers to an antigenic determinant on an antigen to which the paratope of an antibody binds. Epitopic determinants usually consist of chemically active surface groupings of molecules such as amino acids or sugar side chains, and typically have specific three dimensional structural characteristics, as well as specific charge characteristics. Epitopes generally have at least five contiguous amino acids.

The terms "antibody" and "antibodies" include polyclonal antibodies, monoclonal antibodies, humanized or chimeric antibodies, single chain Fv antibody fragments, Fab fragments, and F(ab)$_2$ fragments. Monoclonal antibodies are particularly useful.

In general, a substantially pure consecutive polypeptide comprising the central region of human histidine rich glycoprotein (HRGP) (SEQ.ID.NO: 2), characterised in having anti-angiogenic activity, such as any of the subfragments disclosed by the invention, such as Pep2, or a subfragment of Pep2, which comprises anti-angiogenic activity, is produced recombinantly, by chemical synthesis, or by purification of the native protein, and then used to immunize animals. Various host animals including, for example, rabbits, chickens, mice, guinea pigs, and rats, can be immunised by injection of a subfragment of interest. Adjuvants can be used to increase the immunological response depending on the host species, and include Freund's adjuvant (complete and incomplete), mineral gels such as aluminum hydroxide, surface-active substances such as lysolecithin, pluronic polyols, polyanions, peptides, oil emulsions, keyhole limpet hemocyanin (KLH), and dinitrophenol. Polyclonal antibodies are heterogeneous populations of antibody molecules that are specific for a particular antigen, which are contained in the sera of the immunised animals. Monoclonal antibodies, which are homogeneous populations of antibodies to a particular epitope contained within an antigen, can be prepared using standard hybridoma technology. See Kohler et al. (1975). In particular, monoclonal antibodies can be obtained by any technique that provides for the production of antibody molecules by continuous cell lines in culture, such as the human B-cell hybridoma technique (See Kosbor et al. (1983) and Cole et al. (1983)) or the EBV-hybridoma technique (See Cole et al. (1983)). Such antibodies can be of any immunoglobulin class including IgG, IgM, IgE, IgA, IgD, and any subclass thereof. The hybridoma producing the monoclonal antibodies of the invention can be cultivated in vitro or in vivo.

A chimeric antibody is a molecule in which different portions are derived from different animal species, such as those having a variable region derived from a murine monoclonal antibody and a human immunoglobulin constant region. Chimeric antibodies can be produced through standard techniques.

Humanised forms of the murine antibodies may be made by substituting the complementarity determining regions of the mouse antibody into a human frameworkdomain, by methods known in the art. Selected murine framework residues also may be substituted into the human recipient immunoglobulin. Monoclonal antibodies with a desired binding specificity can be commercially humanised (Scotgene, Scotland; Oxford Molecular, Palo Alto, Calif.). Fully human antibodies, such as those expressed in transgenic animals are also features of the invention. See, for example, Green et al. (1994), U.S. Pat. No. 5,545,806 and U.S. Pat. No. 5,569,825.

Antibody fragments that have specific binding affinity for a substantially pure consecutive polypeptide comprising the central region of human histidine rich glycoprotein (HRGP) (SEQ.ID.NO: 2), or a subfragment thereof, such as any of the subfragments disclosed in the invention, such as Pep2, or a subfragment derived therefrom, characterised in having anti-angiogenic activity, can be generated by known techniques. For example, such fragments include, but are not limited to, F(ab')2 fragments that can be produced by pepsin digestion of the antibody molecule, and Fab fragments that can be generated by reducing the disulfide bridges of F(ab')2 fragments.

Alternatively, Fab expression libraries can be constructed. See, for example, Huse et al (1989). Single chain Fv antibody fragments are formed by linking the heavy and light chain fragments of the Fv region via an amino acid bridge (e.g., 15 to 18 amino acids), resulting in a single chain polypeptide. Single chain Fv antibody fragments can be produced through standard techniques. See, for example, U.S. Pat. No. 4,946,778.

Once produced, antibodies or fragments thereof are tested for recognition of HRGP polypeptides/subfragments, by standard immunoassay methods including, for example, ELISA techniques or RIA. See, Short Protocols in Molecular Biology (1992). Suitable antibodies preferably have equal binding affinities for recombinant and native proteins.

The antibodies of the current invention, generated by using a substantially pure consecutive polypeptide comprising the central region of HRGP, or a subfragment thereof, such as any of the subfragments disclosed by the present invention, such as Pep2, or a subfragment derived therefrom, can be packaged in a diagnostic kit comprising at least one HRGP polypeptide/subfragment specific antibody described herein, which may be conveniently used to detect a HRGP polypeptide/subfragment in a sample for research or diagnostic purposes.

Antibodies to a substantially pure consecutive polypeptide comprising the central region of human histidine rich glycoprotein (HRGP) (SEQ.ID.NO: 2), or a subfragment derived therefrom, such as any of the subfragments disclosed by the present invention, such as Pep2, characterised in having anti-angiogenic activity, may be employed in any known assay method, such as competitive binding assays, direct and indirect sandwich assays, and immunoprecipitation assays. See Zola, Monoclonal Antibodies: A Manual of Techniques (1987).

Competitive binding assays rely on the ability of a labelled standard (which may be a HRGP polypeptide/subfragment, or an immunologically reactive portion thereof) to compete with the test sample analyte (HRGP) for binding with a limited amount of antibody. The amount of HRGP polypeptide/subfragment, in the test sample is inversely proportional to the amount of standard that becomes bound to the antibodies. To facilitate determining the amount of standard that becomes bound, the antibodies generally are insolubilised before or after the competition, so that the standard and analyte that are bound to the antibodies may conveniently be separated from the standard and analyte, which remain unbound.

The HRGP antibodies of the current invention can be neutralising antibodies, capable of substantially inhibiting or eliminating a biological activity of a HRGP polypeptide/subfragment, such as the anti-angiogenic activity of a substantially pure consecutive polypeptide comprising the central region of human histidine rich glycoprotein (HRGP) (SEQ.ID.NO: 2), or a subfragment thereof, such as any of the subfragments disclosed by the present invention, such as Pep2, or a subfragment of Pep2, characterised in having anti-angiogenic activity, as assayed in experiment number 9. The HRGP antibodies of the current invention can also be agonistic or antagonistic of angiogenesis.

The invention further encompasses a method for identifying receptors specific for a substantially pure consecutive polypeptide comprising the central region of human histidine rich glycoprotein (HRGP) (SEQ.ID.NO: 2), or a subfragment derived therefrom, such as any of the subfragments disclosed by the present invention, such as Pep2, or a subfragment of Pep2, characterised in having anti-angiogenic activity, and the receptor molecules identified and isolated thereof. Using techniques well known in the art, a substantially pure consecutive polypeptide comprising the central region of human histidine rich glycoprotein (HRGP), or subfragments thereof, such as any of the subfragments disclosed by the present invention, such as Pep2, or subfragments of Pep2, may be employed to develop affinity columns for the isolation of a receptor from cell lysates. Isolation of a receptor is followed by amino acid sequencing. From this amino acid sequence information, polyR nucleotide probes can be developed for use in cloning polynucleotide sequences that encode a receptor.

A substantially pure consecutive polypeptide comprising the central region of human histidine rich glycoprotein (HRGP) (SEQ.ID.NO: 2), or a subfragment thereof, such as any of the subfragments disclosed by the present invention, such as Pep2, or a subfragment of Pep2, characterised in having anti-angiogenic activity, can be used as a birth control agent by reducing or preventing the uterine vascularisation required for embryo implantation. In such a method of birth control, an amount of a HRGP polypeptide/subfragment, sufficient to prevent embryo implantation is administered to a female mammal. In one aspect of the birth control method, an amount of a HRGP polypeptide/subfragment, sufficient to block embryo implantation, is administered before or after intercourse and fertilization have occurred, thus providing an effective method for birth control, possibly a "morning after" method. Administration methods may include, but are not limited to, pills, injections (intravenous, subcutaneous, intramuscular), suppositories, vaginal sponges, vaginal tampons, and intrauterine devices.

Plasma depleted of polypeptides comprising the central region of human HRGP, or a subfragment thereof, such as any of the subfragments disclosed by the invention, such as Pep2, or a subfragment of Pep2, may be prepared using anti-subfragment/polypeptide HRGP antibodies, such as anti-Pep2 antibodies, or any other anti-subfragment/polypeptide antibodies prepared using any of the subfragments/polypeptides disclosed by the present invention, in various of the art known immunopurification techniques. Such techniques include, but are not limited to, immunoprecipitation, immunoaffinity bead purification and immunoaffinity column chromatography. HRGP polypeptide/subfragment-depleted plasma may also be prepared by passing plasma over a Nicolumn prepared with Ni-NTA agarose resin (Qiagen Inc., Chatsworth, USA), by methods well known in the art.

A typical composition of the present invention comprises a substantially pure consecutive polypeptide comprising the central region of human histidine rich glycoprotein (HRGP) (SEQ.ID.NO: 2), or a subfragment thereof, such as any of the subfragments disclosed by the present invention, such as Pep2, or a subfragment of Pep2, characterised in having anti-angiogenic activity. Furthermore, in some embodiments of the invention, the composition also includes an anti-angiogenic agent and/or an anti-neoplastic agent. In some embodiments, the composition may also include a pharmaceutical carrier.

An anti-angiogenic agent may e.g. be selected from, but is not limited to, interferon-inducible protein 10 and subfragments and analogues of interferon-inducible protein 10, TGF-$\beta$, thrombospondin, IL-1 (interleukin), IFN-$\gamma$ (interferon), IFN-$\alpha$, tissue inhibitor of metalloproteinase-1 (TIMP-1), platelet factor 4 (PF4), protamine, fumagilin, angiostatin and the like.

Furthermore, an anti-neoplastic agent may be included in the composition. Such an anti-neoplastic agent may be a chemotherapeutic agent toxic to tumour cells. Examples of such are alkylating agents, antimetabolites, natural products, hormones and antagonists, biological response modifiers (such as interferon and hematopoietic growth factors), differentiating agents such as butyrate derivatives, antibodies to tumour agents and other miscellaneous agents. Other examples include taxol, cyclophosphamide, carboplatinum, cisplatinum, cisplatin, gancyclovir, campothecin, paclitaxel, hydroxyurea, 5-acacytidine, 5-aza-2'-deoxycytidine, suramin, retinoids and the like.

Furthermore, the combination therapy with a substantially pure consecutive polypeptide comprising the central region of human histidine rich glycoprotein (HRGP) (SEQ.ID.NO: 2), characterised in having anti-angiogenic activity, or a subfragment thereof, such as any of the subfragments disclosed by the invention, such as Pep2, or a subfragment of Pep2, is not limited to an anti-angiogenic agent or an anti-neoplastic agent, but may also include combination treatment methods using an anti-inflammatory agent such as prednisone, a cox-2 inhibitor, and the like. Suitable inflammatory agents may also include ibuprofen and aspirin.

Pharmaceutical compositions comprising a substantially pure consecutive polypeptide comprising the central region of human histidine rich glycoprotein (HRGP) (SEQ.ID.NO: 2), or a subfragment thereof, such as any of the subfragments disclosed by the invention, such as Pep2, or a subfragment of Pep2, characterised in having anti-angiogenic activity, may be administered by intravenous infusion, or may be injected subcutaneously, intramuscularly, intraperitoneally, intrarectally, intravaginally, intranasally, intragastrically, intratracheally, intrapulmonarily, intratumorally or intralesionally.

The dosage depends on physiological factors such as age, weight, the nature of the patients' illness, the patients' sex, etc. The dosage further depends on the route of administration, the nature of the formulation, other drugs being administered and the judgement of the attending physician.

Said patient is selected from the group comprising a mammal, such as human, ape, dog, or rabbit.

A pharmaceutically acceptable carrier is e.g. a biologically compatible vehicle suitable for administration to a mammalian subject. Such pharmaceutically acceptable compositions typically contain from about 0.1 to 90% (such as 1-20% or 1-10%) by weight of a therapeutic agent of the invention in a pharmaceutically acceptable carrier.

Injectable formulations of the composition may contain various carriers such as vegetable oils, dimethylacetamide, dimethylformamide, ethyl lactate, ethyl carbonate, isopropyl myristate, ethanol, polyols (glycerol, propylene glycol, liquid polyethylene glycol and the like).

For intravenous injections, water-soluble versions of the compounds may be administered by a drip method, whereby a pharmaceutical formulation containing HRGP polypeptide/subfragment and a physiological expedient is fused. The physiological acceptable carriers may include, but is not limited to, 5% dextrose, 0.9% saline, Ringer's solution or any other suitable carriers.

Furthermore, intramuscular preparations can be dissolved and administered in a pharmaceutical excipient such as 0.9% saline or 5% glucose solution.

For a topical administration, a semi-solid ointment formulation typically contains a formulation of the active ingredient from about 1 to 20% e.g. 5 to 10%, in a carrier such as a pharmaceutical cream base. Formulations for topical use include, but is not limited to, creams, solutions, tinctures, drops, lotions and ointment which comprise the active ingredient and various supports and vehicles. The optimal percentage of the therapeutic agent in each pharmaceutical formulation varies according to the formulation itself and the therapeutic effect, which is desired in the specific pathologies and correlated therapeutic regiments. Methods of making such formulations can be found in "Remingtons Pharmaceutical Sciences"

An insoluble form of the compound may be prepared and administered as a suspension in an aqueous base or a pharmaceutically acceptable oil base, such as an ester of a long acid fatty chain (e.g. ethyl oleate).

The amount of a pharmaceutical that is desirable to produce a medical effect in a treated mammal (e.g. human) is specified as a "therapeutically effective amount". Accordingly, the dosage for any patient depends on many factors, including the patients age, sex, body surface area, the particular compound to be administered, the patients' general health, route of administration, and also other drugs being administered concurrently. The preferred administration will most likely be intravenous.

In one embodiment, a substantially pure consecutive polypeptide comprising the central region of human histidine rich glycoprotein (HRGP) (SEQ.ID.NO: 2), or a subfragment thereof, such as any of the subfragments disclosed by the present invention, such as Pep2, or a subfragment of Pep2, characterised in having anti-angiogenic activity, will be administered to a patient who is suffering from a disease state were it is desired to inhibit angiogenesis. In another embodiment, a pro-angiogenic subfragment thereof may be administered to a patient who is suffering from a condition were it is desired to promote angiogenesis.

Appropriate treatment subjects include, without limitation, those patients suffering from an angiogenesis-related condition, such as for example angiogenesis-related cancers rhabdomyosarcoma, glioblastoma multiforme, leiomyosarcoma, prostate carcinoma, mammary carcinoma, lung carcinoma, melanoma, bladder carcinoma, pancreatic carcinoma and renal carcinoma, were a treatment with an anti-angiogenic agent is preferable.

Furthermore, patients suffering from an angiogenesis-related condition such as, but not limited to, diabetic retinopathy, diabetic neovascularization, retrolental fibroplasias, trachoma, neovascular glaucoma, psoriasis, angio-fibromas, immune and non-immune inflammation, capillary formation within atherosclerosis plaques, myocardial angiogenesis, hemangiomas, excessive wound repair, various inflammatory diseases and any other disease characterised by excessive and/or deregulated anglogenesis, may benefit from a treatment with a substantially pure consecutive polypeptide comprising the central region of human HRGP (SEQ.ID.NO: 2), or a subfragment thereof, such as any of the subfragments disclosed by the present invention, such as Pep2, or a subfragment of Pep2, characterised in having anti-angiogenic activity.

FIGURE LEGENDS

FIG. 1. Human HRGP inhibits CAM angiogenesis.
  A. Structurally HRGP can be divided into three main domains; the N-terminus with two cystatin-like stretches, a histidine-proline-rich (His/Pro-rich) middle domain and the C-terminus. Both the His/Pro-rich middle domain and the C-terminus are disulfide bonded to the N-terminal part of the protein.
  B. HRGP was obtained from three different sources; either purified from human plasma (pHRGP) or recombinantly produced, with or without a His-tag (His-HRGP and rHRGP, respectively). Both Coomassie staining and Western blot (WB) with an HRGP-specific antibody revealed, except for the full length protein at approximately 75 kDa, a number of smaller subfragments.
  C. FGF-induced angiogenesis in the chicken CAM was effectively inhibited in the presence of HRGP.

Figure 2:
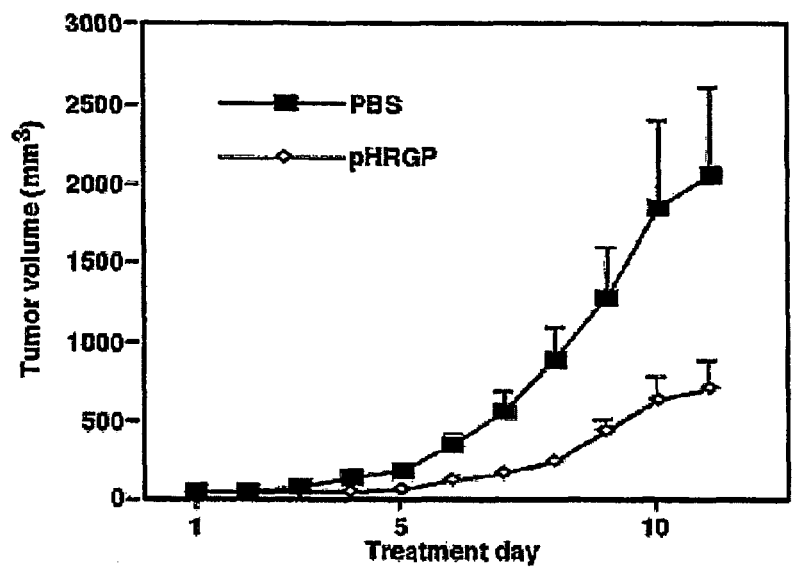
Figure 2:
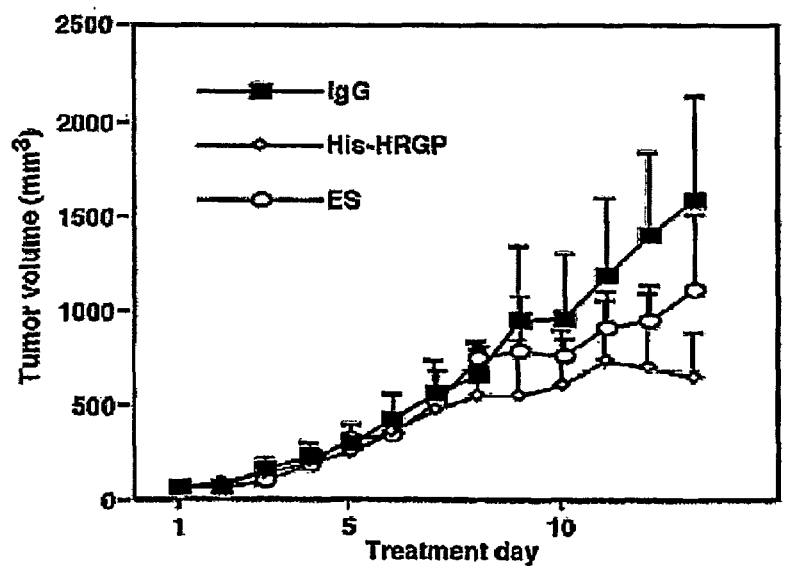
Figure 2:
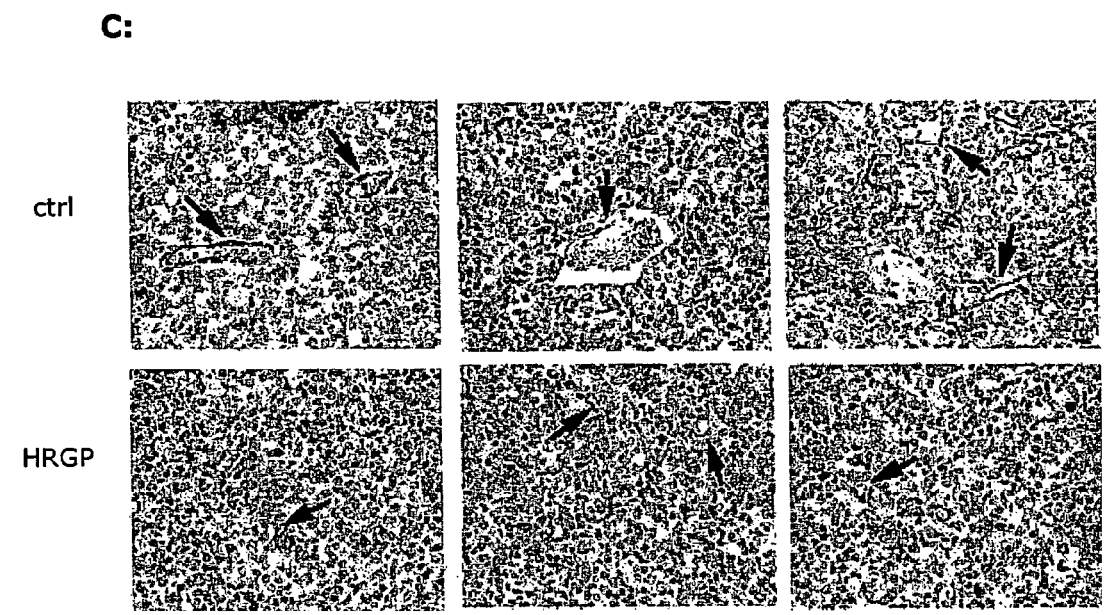
Figure 2:
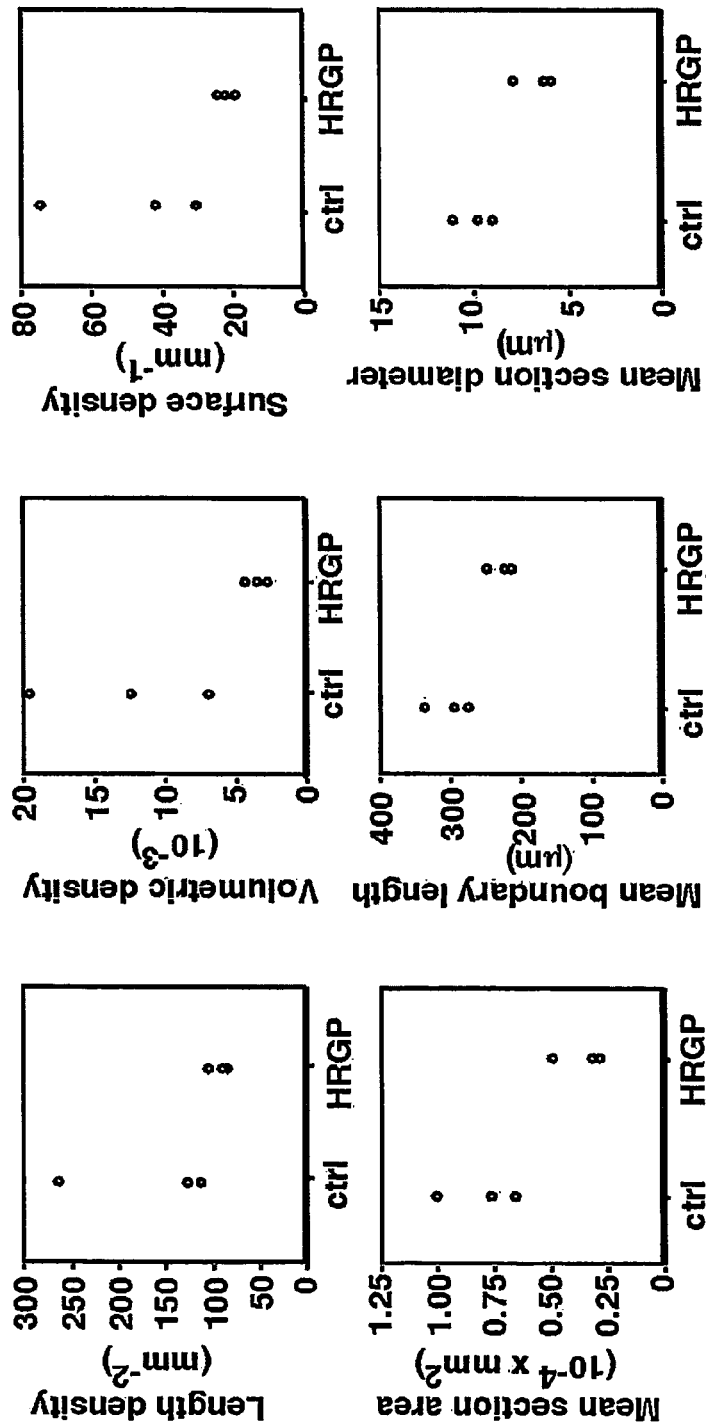

FIG. 2. HRGP inhibits tumour growth and vascularization.
  Mice bearing palpable fibrosarcoma tumours were treated daily with s.c. injections of either pHRGP or PBS (A) or His-HRGP, human IgG (B) and the tumour volume was measured daily with a caliper. Endostatin (ES) was included in one study for comparison (B). C. Staining for CD31 on paraffin-sections of the tumours from mice treated with either IgG (ctrl) or HRGP. Arrows indicate vessels. D. Stereological quantification of vascular parameters in three tumours from IgG- (ctrl) or HRGP-treated mice. Individual values from each tumour is indicated with a circle.

Figure 3:
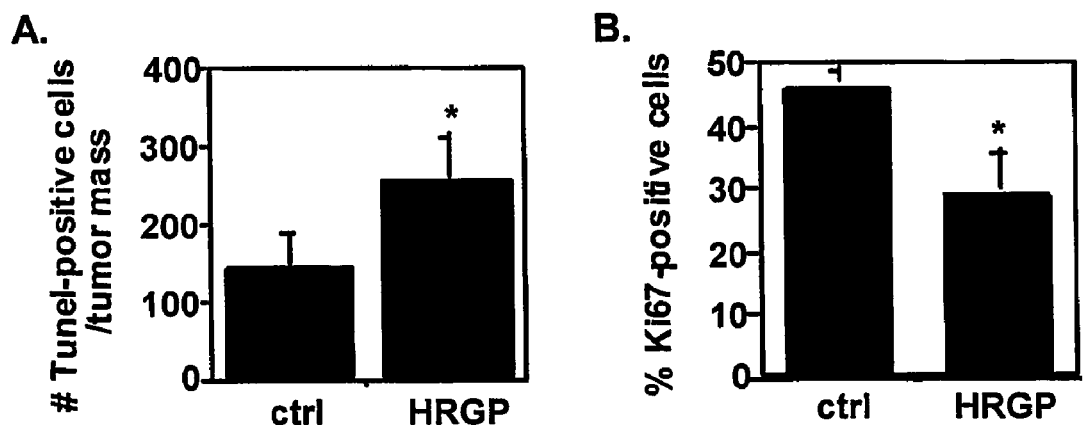

FIG. 3. Decreased proliferation in tumours from HRGP-treated mice.
  Paraffin-sections of tumours from HRGP- or IgG (ctrl)-treated mice were stained for A. apoptotic (TUNEL-positive) and B. proliferating (Ki67-positive) cells. The proportions are expressed as number of positively stained cells per total number of cells counted. * denotes $P<0.05$.

Figure 4:
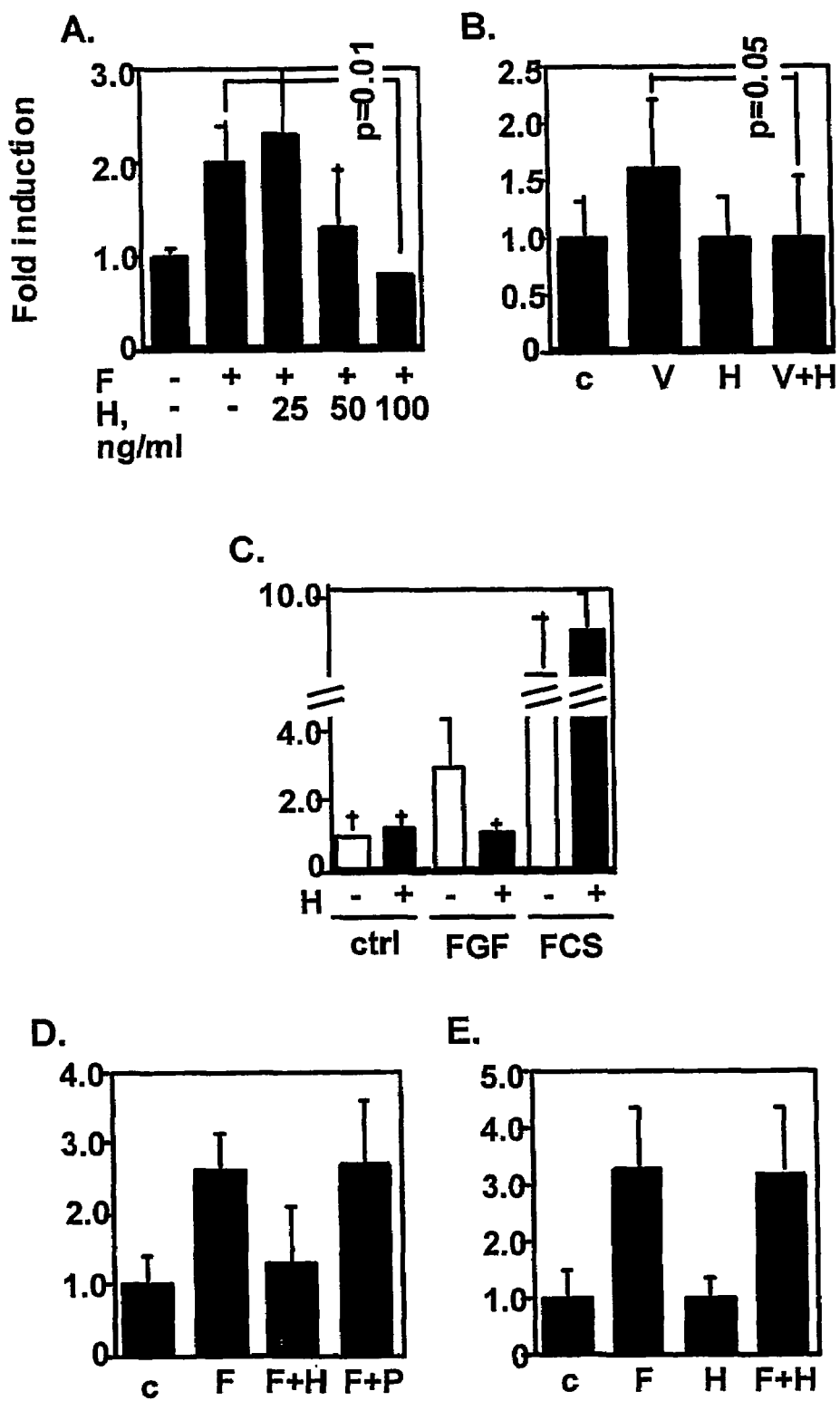

FIG. 4. HRGP inhibits chemotaxis of primary endothelial cells.
  A. Chemotaxis of primary BCE cells induced by FGF-2 (F) was completely arrested in the presence of 100 ng/ml HRGP (H).
  B. The same concentration of HRGP also inhibited VEGF-A (V)-induced chemotaxis.
  C. However, FCS-induced chemotaxis of BCE cells was not inhibited in the presence of HRGP.
  D. PCI (P) had no effect on FGF-2-induced chemotaxis of BCE cells.
  E. FGF-2-induced chemotaxis of NIH 3T3 murine fibroblasts was not inhibited by HRGP.

Figure 5:
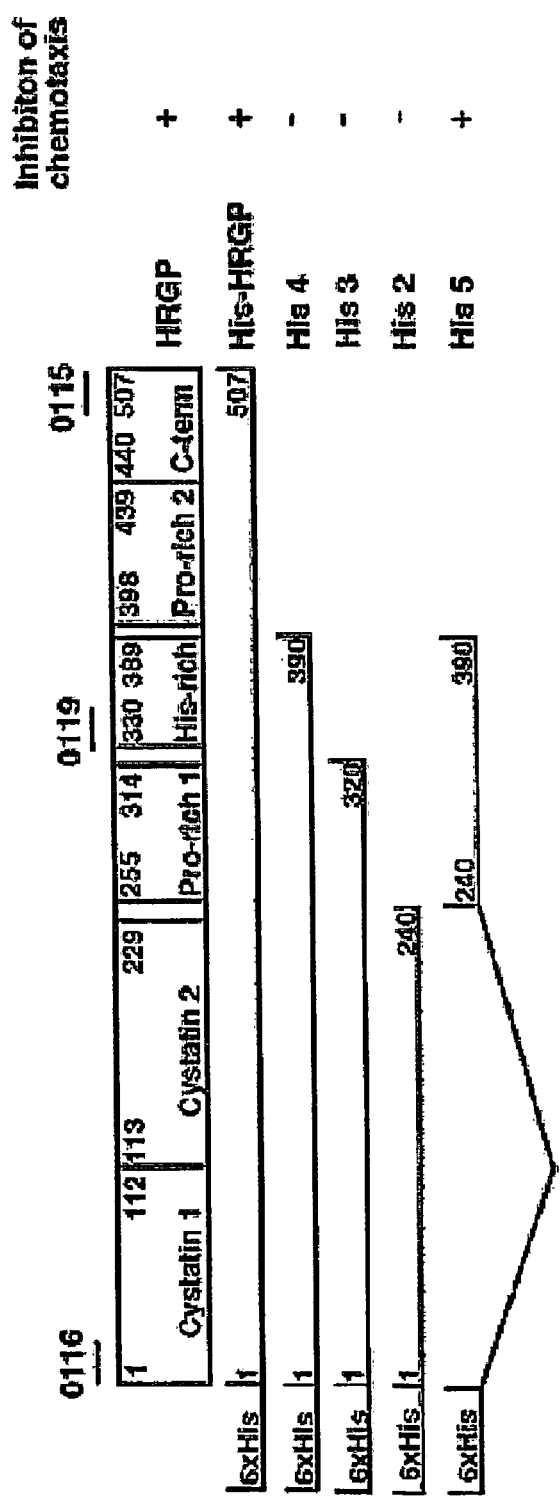
Figure 5:
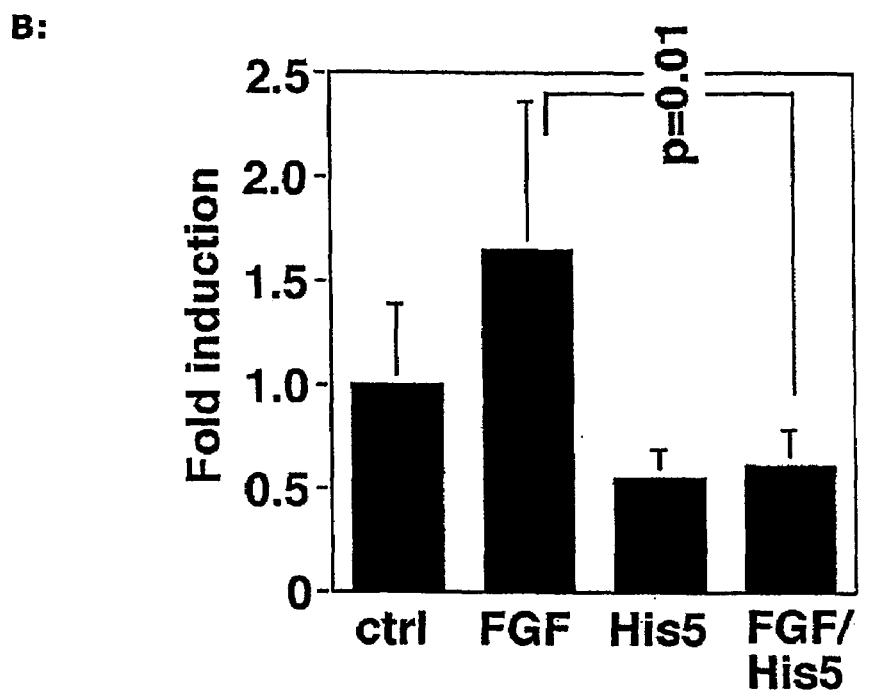
Figure 5:
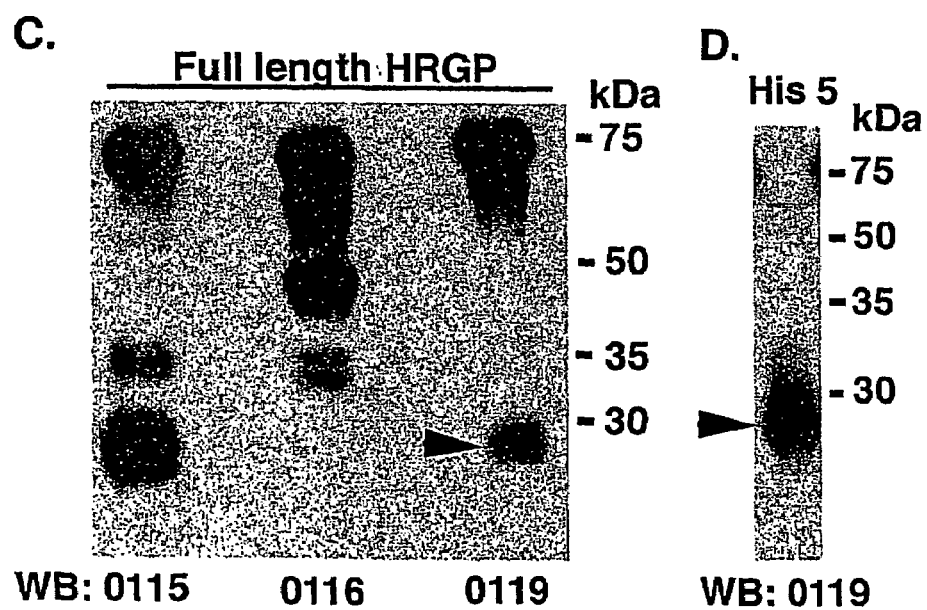

FIG. 5. The His/Pro-rich domain of HRGP inhibits chemotaxis.
  A. Schematic overview of HRGP and truncated versions (His 2-5). The ability to inhibit FGF-2-induced chemotaxis of endothelial cell is indicated by +/− (6xHis tag disclosed as SEQ ID NO: 29).
  B. Quantification of the inhibitory effect of His 5 on FGF-2 induced chemotaxis of endothelial cells.
  C. Western blot (WB) of mature HRGP using the peptide antibodies 0115, 0116 and 0119 gives different patterns of immunoreactivity (10% SDS-PAGE).
  D. Western blot of the subfragment His 5 using antibody 0119 yields immunoreactivity with one peptide migrating around 30 kDa (12.5% SDS-PAGE).

Figure 6:
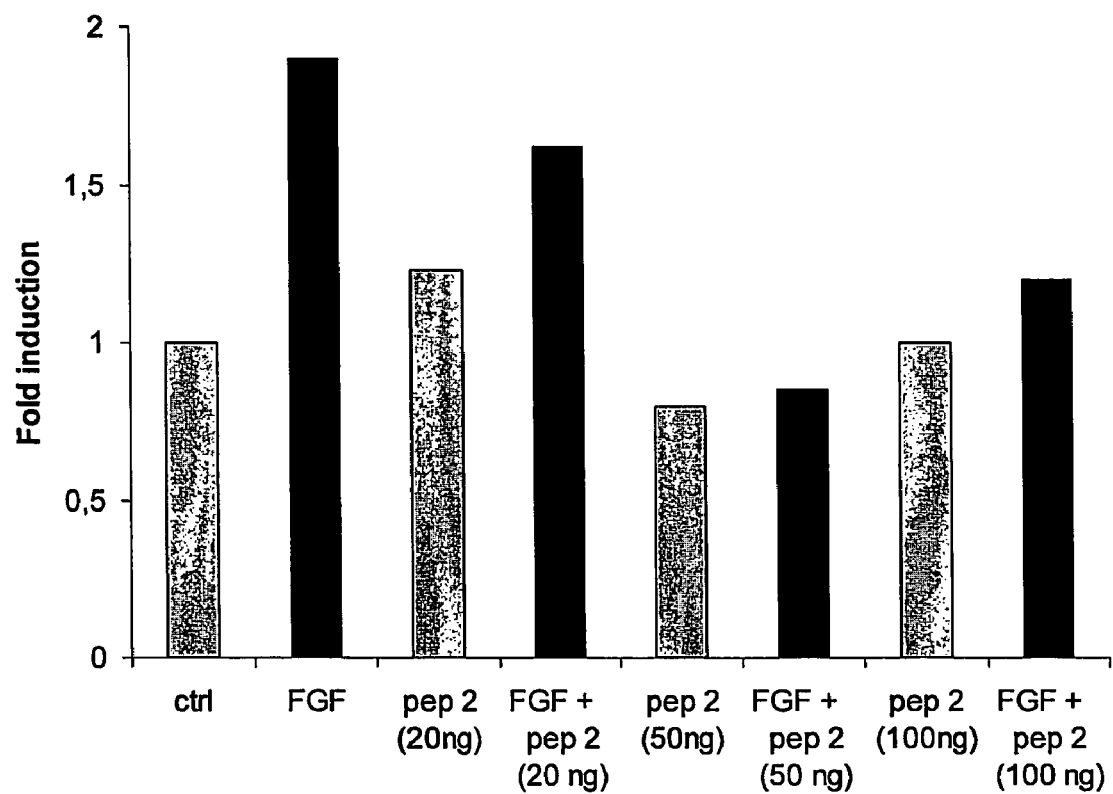

FIG. 6: Dose response study of Pep2
  Chemotaxis of primary BCE cells induced by FGF-2 was dose-dependently inhibited by Pep 2.

Figure 7:
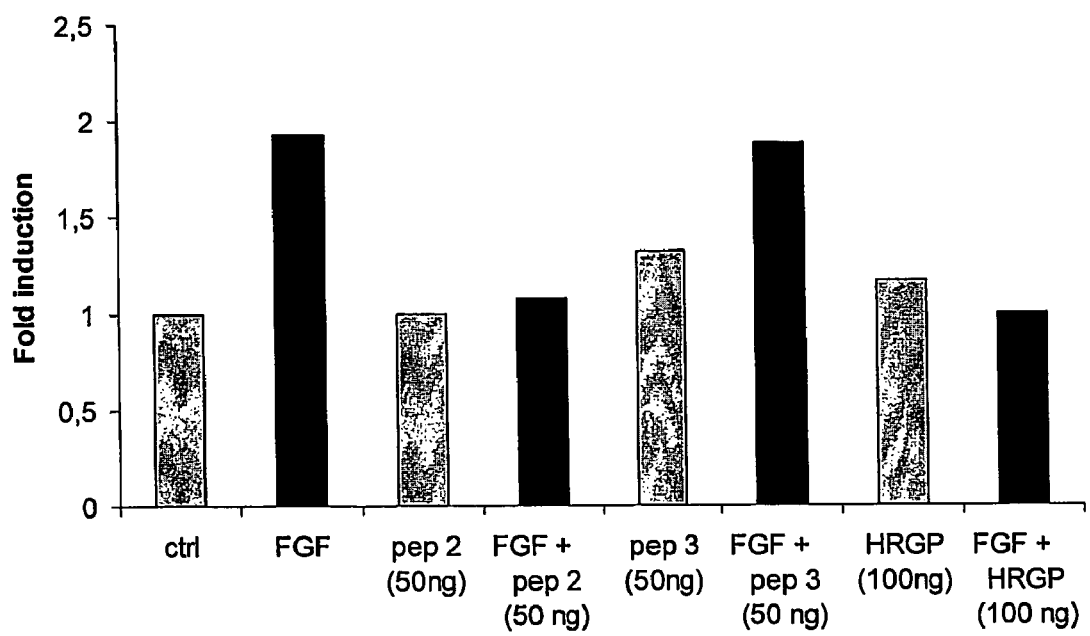

FIG. 7: Comparative study Pep2lPep3
  Chemotaxis of primary BCE cells induced by FGF-2 was inhibited by HRGP (100 ng/ml) and Pep 2 (50 ng/ml) but not by Pep 3 (50 ng/ml).

Figure 8:
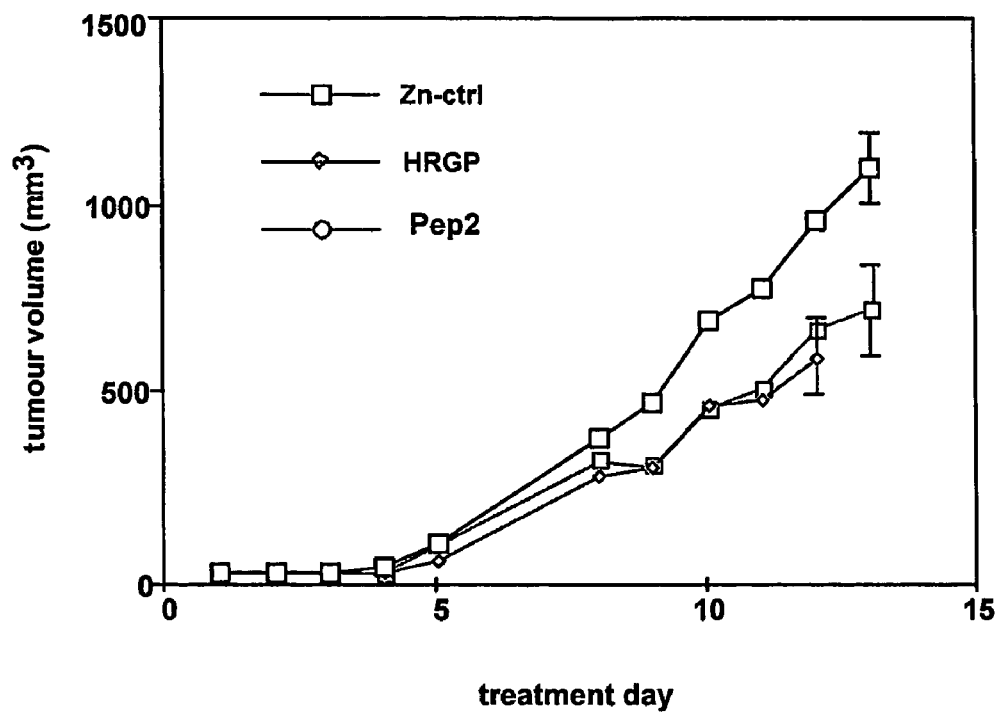

FIG. 8: Pep2 inhibits tumor growth
  Mice bearing palpable fibrosarcoma tumours were treated daily with s.c. Injections of either vehicle (Zn-acetate in NaCl), 5 mg/kg/day of Pep 2, or 5 mg/kg/day of full-length HRGP and the tumour volume was measured daily with a caliper.

Figure 9:
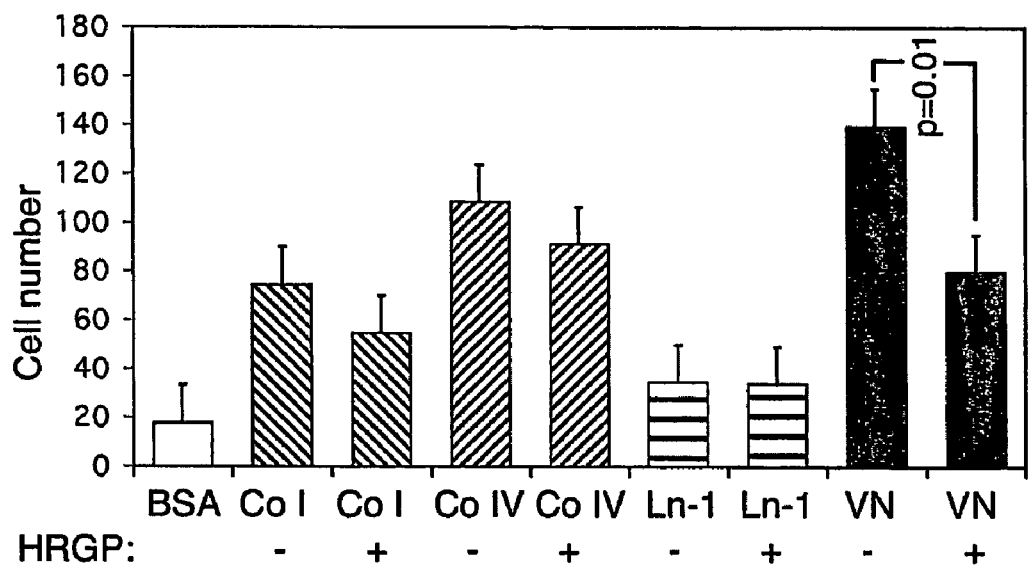

FIG. 9: HRGP decreases endothelial cell adhesion to vitronectin, collagen I and collagen IV.
  BCE cells were seeded in serum-free medium, with or without HRGP (100 ng/ml), allowed to adhere to wells coated with collagen I (Co I), collagen IV (Co IV), laminin-1 (Ln-1) and vitronectin (VN). Non-adherent cells were removed by washing and the remaining cells were counted. Error bar indicates one standard deviation.

Figure 10:
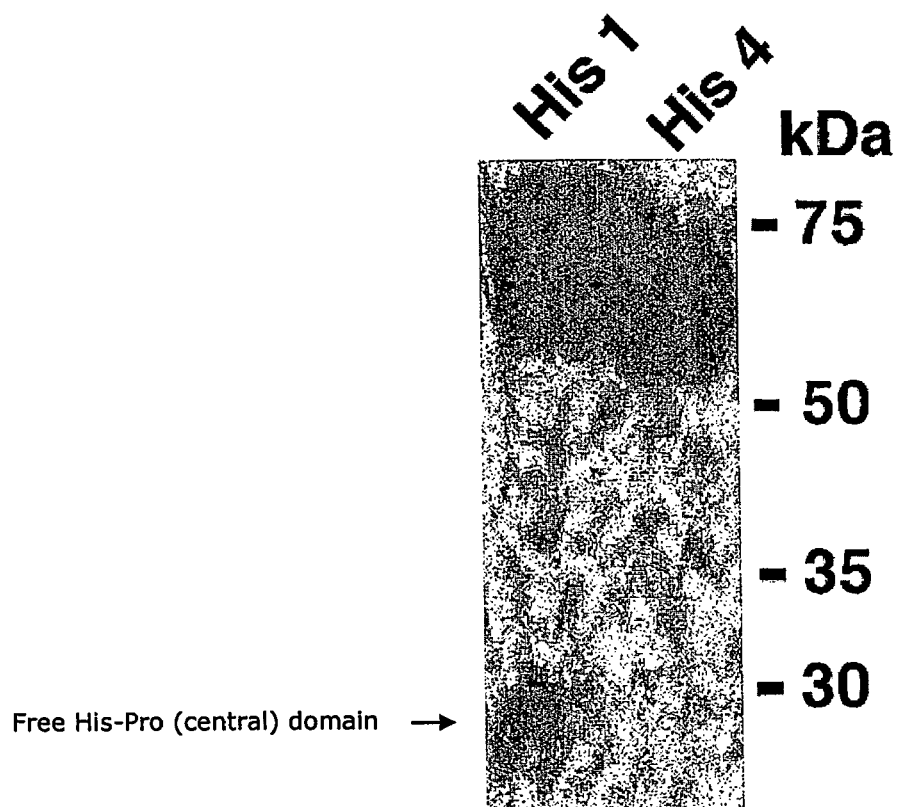

FIG. 10: The central region (His/Pro domain) is active only when released from HRGP.
  The failure of His4 to inhibit endothelial cell chemotaxis in spite of that this protein contains the His/Pro domain of HRGP was analyzed by SDS-PAGE and immunoblotting of purified protein. Blotting with the 0119 rabbit antiserum, which recognizes the His/Pro domain showed that the His/Pro domain was released from His1, the full length protein, but not from His4. We conclude that the His/Pro domain has to be released from HRGP protein to allow inhibition of endothelial cell chemotaxis.

Figure 11:
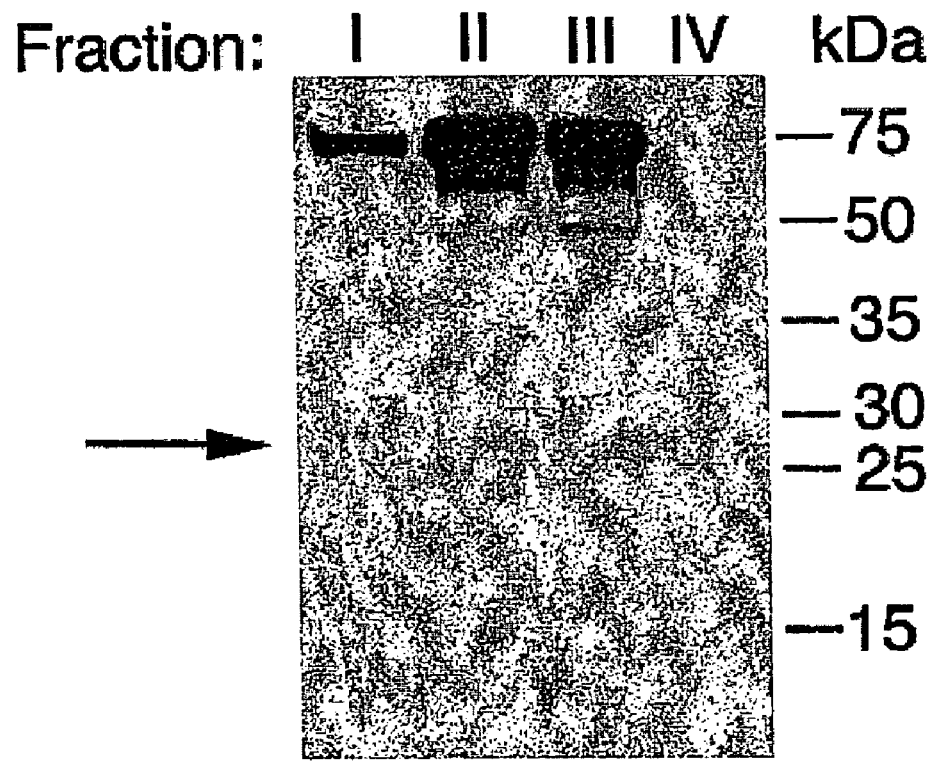

FIG. 11: The central region (His/Pro domain) of HRGP exists as a circulating fragment in serum.
  Fresh serum was collected and purified by use of affinity chromatography on purified 0119 antibody immobilized on Sepharose. Eluted material was collected in fractions and analyzed by SDS-PAGE and immunoblotting using the 0119 antiserum against the His/Pro domain. Arrow points to the immunoreactive, free, His/Pro domain-containing fragment.

FIG. 12: HRGP, or a central region fragment of HRGP is deposited in the vessel basement membrane.
  Human normal kidney was sectioned and immunostained using purified 0119 antibody in combination with Ulex Europeus Agglutinin (UEA). Immunoreactivity mediated by the 0119 antibody is shown in red and UEA-reactivity in green (grey and light grey in black and white picture, respectively). The panel to the right shows merged picture to illustrate overlapping reactivity.

EXPERIMENTS

Experiment 1

Tissue Culture

Procedure

The porcine aortic endothelial (PAE) cell line overexpressing FGF receptor-1 (FGFR-1) (Wennström et al 1992) was cultured in Ham's F12/10% fetal bovine serum (FCS) and NIH 3T3 murine fibroblasts were cultured in Dulbecco's modified medium (DMEM)/10% newborn calf serum (NCS). F12, DMEM and serum were bought from Life Technologies. Primary bovine adrenal cortex capillary endothelial (BCE) cells were cultured on gelatin-coated dishes in DMEM/10% NCS and 2 ng/ml FGF-2 (Boehringer Mannheim). For chemotaxis assays, both PAE and NIH 3T3 cells were serum-starved over night in 0.1% BSA and BCE cells in 0.5% NCS. Human embryonic kidney (HEK) 293-EBNA cells were cultured in DMEM/10% FCS. Approximately every second month they were given 0.25 mg/ml G418 (Calbiochem) to ensure positive selection of the EBNA-1 expressing cells.

Experiment 2

HRGP Expression Vectors, Transfection and Purification of Protein

HRGP from three different sources were used in this study; HRGP purified from human plasma (pHRGP) and recombinant HRGP produced in HEK-293-EBNA cells, with or without a His-tag (His-HRGP and rHRGP, respectively).

Procedure

Full length cDNA encoding human HRGP including the signal sequence (amino acid residues 1-18) was cloned into the pCEP-Pu2 (Vernersson et al 2002) expression vector. Expression vectors for His-tagged HRGP variants were also constructed using the same vector. The truncations were produced by PCR-amplification of shorter parts of the protein. N-terminally of the HRGP coding region, a His-tag (six histidine residues (SEQ ID NO: 29)) was added to enable purification. An enterokinase cleavage site was introduced between the His-tag and the HRGP coding region, to allow removal of the His-tag. In these vectors, the HRGP signal sequence was excluded and instead, the PCR-product was ligated in frame with the BM40 signal sequence in pCEP-Pu2.

HEK 293-EBNA cells were used to produce the recombinant HRGP. These cells are stably transfected with the EBNA-1 gene, which is also expressed by the pCEP-Pu2 vector, to efficiently prevent chromosomal integration of transfected plasmid DNA, resulting in an overall high yield of recombinant protein, without the need for characterization of individual clones. The HRGP expression vectors were transfected into the 293-EBNA cell line using Lipofectamine™ (Invitrogen) and selected with 2.5 mg/ml puromycin (Sigma). To avoid contamination of bovine HRGP in the conditioned medium, a defined serum-replacement medium, TCM™ (ICN Biomedicals) was used instead of FCS.

Chromatography on phosphocellulose (Kluszinsky et al 1997, Rylatt et al 1981) in the presence of proteinase inhibitors was used to purify HRGP from freshly collected human plasma (pHRGP), or recombinant untagged HRGP from conditioned medium (rHRGP). His-tagged HRGP was purified using Ni-NTA agarose (Qiagen) according to the manufacturer's protocol. Protein-containing fractions were pooled and dialysed against PBS pH 7.4.

Results

Recombinant untagged HRGP migrates with an apparent lower molecular mass on SDS-PAGE than HRGP purified from plasma (FIG. 1B), probably reflecting different levels of glycosylation. This difference in migration rate between endogenous and recombinant protein is not apparent when comparing pHRGP and His-HRGP (FIG. 1B), due to the addition of 10 extra amino acid residues to His-HRGP (providing a His-tag and enterokinase cleavage site to enable removal of the tag). Western blotting with an HRGP-specific antibody, revealed apart from the full-length protein, a number of smaller subfragments in all three purified fractions (FIG. 1B). These subfragments are most likely degradation products of HRGP, since mass-spectrometry analysis failed to reveal any contaminating peptides.

Experiment 3

HRGP Inhibits CAM Angiogenesis

The effect of HRGP on anglogenesis was tested in the chicken chorioallantoic membrane (CAM) assay.

Procedure

The conditions for the chorioallantoic membrane (CAM) assay followed essentially a previously described procedure (Friedlander et al (1995), Dixelius et al, (2000)). FGF-2 (Boehringer Mannheim) and VEGF-A (Peprotech) was used at 0.2 mg per filter and purified pHRGP or rHRGP at 3 mg per filter. The treated CAM's were inspected in a light microscope and the score, from 0 (low) to 3 (high) was based on the number of vessel branch points. Average values for 5-6 embryos were recorded.

Results

A filter disc soaked in vehicle or growth factor, with or without HRGP, was placed on top of the CAM in the vicinity of a large vessel and incubated for three days. Treatment of the CAM with growth factors, such as FGF-2, stimulated angiogenesis (FIG. 1C; Table 1). Application of FGF-2 or VEGF-A together with pHRGP on the CAM led to an efficient suppression of newly formed vessels, whereas pre-established vessels remained unaffected during these conditions. The same result was obtained using rHRGP (data not shown).

Experiment 4

Animal Studies

HRGP Inhibits Tumour Growth in Mice Due to Decreased Proliferation

Angiogenesis plays an important role in the growth of aggressive tumours, therefore the effect of HRGP on fibrosarcoma growth in mice was investigated, using both pHRGP (FIG. 2A) and His-HRGP (FIG. 2B). To determine the mechanism whereby HRGP treatment reduced tumour growth, the proportion of apoptotic and proliferating cells in tumour tissue from the two treatment groups was further quantified.

Procedure

Animal work was carried out at the local animal facility and was approved by the Uppsala University board of animal experimentation and thus performed according to the UKC- CCR guidelines for the welfare of animals in experimental neoplasia (Workman et al (1988)). The mice were anesthetized with isoflurane (Forene; Abbott) during all manipulations. Female, 5 week old, C57BL6/1 mice (Mollegard/Bomhultgard, Denmark) were injected with 0.5×106 T241 fibrosarcoma cells subcutaneously (s.c.) into the left flank. Animals carrying palpable tumours were randomized (n=7-10 animals/treatment group) and received treatment with vehicle (PBS), 4 mg/kg/day of pHRGP or 5 mg/kg/day of human IgG or His-HRGP, given as daily subcutaneous injections in the right flank. The tumours were measured with a caliper once a day, in a blind procedure, and volumes were calculated by the formula P/6×width×length. When the tumours reached the upper limit of 2 $cm^3$, the mice were sacrificed. Three animals in each group were perfused with 4% paraformaldehyde in PBS pH 7.4. Tumours were embedded in paraffin according to standard histological procedures and sectioned at 4 mm thickness.

Results

C57/bl6 mice were inoculated subcutaneously with T241 fibrosarcoma cells on their left flank and when the tumours were palpable (after 4-6 days), a daily treatment was initiated with HRGP or control (PBS; FIG. 2A, or human IgG; FIG. 2B). Endostatin was included in one study for comparison (FIG. 2B). The treatment was given as subcutaneous injections in the right flank until the size of the control tumours reached the upper limit of 2 $cm^2$ (11 days; FIG. 2A, 14 days; FIG. 2B). Injections with both pHRGP (4 mg/kg/day) and His-HRGP (5 mg/kg/day) led to a drastic reduction in tumour growth and at the time of sacrifice, the size of the tumours was reduced by 67% (FIG. 2A) and 61% (FIG. 2B) respectively, compared to control-treated animals. Endostatin treatment (25 mg/kg/day) lacked significant inhibitory effect on tumour growth in this model (32% decrease).

Apoptotic cells were visualized by TUNEL staining. No difference in tumour apoptosis could be found between the two groups (FIG. 3A) and the percentage of apoptotic cells in the tumours was generally low (less than 1%) in both groups. The proportion of proliferating cells was determined by immunohistochemical staining for the Ki67 antigen. As shown in FIG. 3B, there were significantly less proliferating cells in the tumours from HRGP-treated mice compared to those from control-treated animals; 29% and 43% respectively.

Experiment 5

Reduced Vascularization in Tumours from HRGP-treated Mice

Mice treated with HRGP show a reduced vascularization pattern in tumours, as shown in an immunostaining of paraffin-section of tumours.

Procedure

Paraffin-sections of tumours from control- or HRGP-treated animals were immunohistochemically (IHC) stained for CD31 and Ki67 using a goat anti-mouse CD31 antibody (1506; Santa Cruz), diluted 1:500 and incubated at +4° C. over night, and a rat anti-mouse Ki67 antibody (TEC-3/M7249; DAKO) diluted 1:50 and incubated for 30 min. at room temperature, according to standard IHC procedures. Detection of apoptotic cells by the TUNEL-technique was performed using ApopTag™ (Intergen Company) according to the manufacturer's protocol. Stereological quantification of vascular parameters was performed as described earlier by Weibel et al (1979) and Gundersen et al (1988). Quantification of the relative number of Tunel- and Ki67-positive cells was calculated from approximately 3000 cells per tumour section, in three tumours from each treatment group. Significance at the level of $P<0.05$ was calculated using Students t-test.

Results

Sections of paraffin-embedded tumours from control (IgG)- or HRGP-treated mice were immunohistochemically stained for CD31 expression to visualise the vessels. Visual inspection revealed clear changes in the extent of vascularisation of the treated tumours compared to control, in particular with regard to the reduced vessel diameter in response to HRGP treatment (FIG. 2C). Stereological quantification of vascular parameters was performed as described earlier by Weibel et al (1979) and Gundersen et al (1988). This method of quantifying tumour angiogenesis relates the length, volume and surface area of the vessels to tumour volume. The results show that all six vascular parameters determined were reduced in tumours from HRGP-treated mice (FIG. 2D).

Experiment 6 A

HRGP Inhibits Chemotaxis of Primary Endothelial Cells

HRGP acts through the inhibition by chemotaxis of endothelial cells, which is a common feature of anti-angiogenic molecules.

Procedure

A migration assay was performed in a modified Boyden chamber as described earlier (Auerbach et al., 1991) using micropore polycarbonate filters (8 μm thick, 8 μm pore) coated with type-1 collagen solution at 100 μg/ml (Vitrogen 100, Collagen Corp). BCE, PAE/FGFR-1 or NIH 3T3 cells were preincubated or not with HRGP (100 ng/ml) for 30 min, trypsinised and resuspended at a concentration of $7.5×10^5$ cells/ml in Dulbecco's modified essential medium (Invitrogen) containing 0.25% BSA and Trasylol at 1000 KIE. FGF-2 and VEGF-A was used at 5 ng/ml, HRGP and the protein C inhibitor (PCI) at 100 ng/ml and BSA at 0.25%. After 5 h at 37° C., migrated cells were stained with Giemsa and counted using an image analysis software (Easy Image Analysis) from Tekno Optik AB, Sweden. All samples were analysed in at least six parallel wells for each treatment.

Preparation and $Zn^{2+}$-Loading of Peptides

Peptides were bought from Innovagen AB, 22 370 Lund, Sweden and delivered dried in glass vials. Peptides were weighed out and dissolved in phosphate buffered saline to a concentration of 1 mg/ml. A solution of 10 mM $ZnCl_2$ in destilled $H_2O$ was prepared. Peptides were incubated with a 10-fold molar excess of the peptide for 30 min, or alternatively, $ZnCl_2$ to a final concentration of 5 mM was included in the cell suspension added to both wells of the Boyden chamber assay, as described above.

Results

A common feature of the anti-angiogenic molecules described to date is their ability to inhibit chemotaxis of endothelial cells in vitro. In accordance, inclusion of 100 ng/ml of rHRGP completely blocked FGF-2-induced chemotaxis of BCE cells as shown in FIG. 4A. The same concentration of rHRGP also attenuated VEGF-A-induced chemotaxis (FIG. 4B). However, chemotaxis induced by FCS was not inhibited by rHRGP (FIG. 4C). To demonstrate specificity, another plasma protein of approximately the same mass as HRGP, the protein C inhibitor (PCI), was included for comparison. PCI had no effect on FGF-2-induced chemotaxis (FIG. 4D). The specificity of HRGP towards endothelial cells was implied by the fact that FGF-2-induced chemotaxis of NIH 3T3 murine fibroblasts was not affected by the presence of rHRGP (FIG. 4E).

Experiment 6B

The Central Region (His/Pro-rich Domain) of HRGP Inhibits Chemotaxis

Procedure/Results

To determine which part of HRGP was responsible for the anti-angiogenic effect, recombinant truncated forms of the protein were produced (FIG. 5A). Truncated versions containing the C-terminal part of HRGP, but lacking an intact N-terminus, were not possible to produce, maybe due to instability. Of the four truncated proteins tested (His 2-5), only the His/Pro-rich domain (His 5) inhibited chemotaxis of endothelial cells towards FGF-2 (see +/−indications in FIG. 5A).

Experiment 7

The Central Region (His/Pro-rich Domain) as a Naturally Occurring Degradation Product of HRGP HRGP is proteolytically cleaved from full-length protein to smaller subfragments when purified from plasma. One subfragment from the His/Pro region is suggested to comprise the full activity of the protein (minimal functional entity), this could be a naturally occurring subfragment.

Procedure

Purified HRGP was separated on 10% (pHRGP, rHRGP and His-HRGP) or 12.5% SDS-PAGE (His 5). The monoclonal mouse anti-human HRGP antibody M037 (Takara) was used at 0.05 mg/ml and the rabbit polyclonal peptide antibodies 0115, 0116 and 0119 were used at a 1:5000 dilution. For detection of His-tagged proteins an anti-penta His (SEQ ID NO: 30) antibody, directly conjugated to HRP (34460; Qiagen) was used at 1:5000 dilution.

Results

Domain-specific antibodies against HRGP were raised by immunizing rabbits with three different peptides; 0115, 0116 and 0119. The positions of these peptides in the HRGP protein are indicated in FIG. 5A. Western blot of full length HRGP with the three peptide-antibodies revealed apart from the full length protein, a specific pattern of reactivity with smaller HRGP-derived subfragments (FIG. 5C). Interestingly, the apparent molecular weight of 30 kDa of the His/Pro-rich subfragment (His 5) equals that of a naturally occurring HRGP subfragment recognized by the antibody 0119, directed against the His/Pro-rich domain of HRGP (FIG. 5C). This indicates the possibility that the His/Pro-rich domain in human HRGP may be proteolytically released from the full-length protein in vivo.

Experiment 8

Dose Response Study Pep2

A migration assay was performed in a modified Boyden chamber as described earlier (Auerbach et al., 1991) using micropore polycarbonate filters (8 μm thick, 8 μm pore) coated with type-1 collagen solution at 100 μg/ml (Vitrogen 100, Collagen Corp). BCE Cells were trypsinised and resuspended at $7.5 \times 10^5$ cells/ml in Dulbecco's modified essential medium (Invitrogen) containing 0.25% BSA and Trasylol at 1000 KIE. The cell suspension was added in the upper chamber and FGF-2 (10 ng/ml), and/or peptide 2 (20, 50 or 100 ng/ml) in medium containing 0.25% BSA were added to the lower chamber. The peptides were dissolved in PBS containing a 10-fold molar excess (Zn:peptide) of $Zn^{2+}$-acetate. After 5 h at 37° C., cells that had migrated through the filter were stained with Giemsa and counted using an the Easy Image Analysis software. All samples were analysed in at least six wells for each treatment and at several separate occasions. The outcome of the study is shown in FIG. 6.

Experiment 9

Comparative Study pep2/pep3: Chemotaxis

Primary endothelial cells were starved over night in 0.5% normal calf serum. A migration assay was performed in a modified Boyden chamber as described earlier (Auerbach et al., 1991) using micropore polycarbonate filters (8 μm thick, 8 μm pore) coated with type-1 collagen solution at 100 μg/ml (Vitrogen 100, Collagen Corp). Cells were trypsinized and resuspended at $7.5 \times 10^5$ cells/ml in Dulbecco's modified essential medium (Invitrogen) containing 0.25% BSA and Trasylol at 1000 KIE. The cell suspension was added in the upper chamber and FGF-2 (10 ng/ml), HRGP (100 ng/ml), peptide 2 or 3 (50 ng/ml) in medium containing 0.25% BSA were added to the lower chamber. The peptides were dissolved in PBS containing a 10-fold molar excess (Zn:peptide) of $Zn^{2+}$-acetate. After 5 h at 37° C., cells that had migrated through the filter were stained with Giemsa and counted using the Easy Image Analysis software. All samples were analyzed in at least six wells for each treatment. Results of the study are illustrated in FIG. 7.

Experiment 10

Animal Study Pep2

Procedure

Tumour study: Female, 5 week old, C57BL6/J mice (Mollegard/Bomhultgard, Denmark) were injected with $0.5 \times 10^6$ T241 fibrosarcoma cells subcutaneously (s.c.) into the left flank. Animals carrying palpable tumours were randomised (n=5-10 animals/treatment group) and received treatment with vehicle (Zn-acetate in NaCl), 5 mg/kg/day of HIS1 (=full-length HRGP) or Pep2, in a volume of 100 microliters, given as s.c. injections daily, in the right flank. The tumours were measured with a caliper once a day, in a blind procedure, and volumes were calculated by the formula $n/6 \times width^2 \times length$. When the tumours reached the upper limit of 2 $cm^3$, the mice were sacrificed. The animals were anesthetised with isoflurane (Forene; Abbott) during all manipulations. The results are shown in FIG. 8.

Experiment 11

Adhesion

BCE cells were detached using non-enzymatic "Cell Dissociation Solution" (Sigma), washed and re-suspended in DMEM/0.1% BSA and FGF-2 (2 ng/ml). The cells were seeded in serum-free medium, with or without HRGP (100 ng/ml), into wells pre-coated with BSA, collagen I, collagen IV, laminin-1 or vitronectin, respectively (CytoMatrix ECM 205 kit, Chemicon). The cells were incubated for 45 (collagen I, collagen IV and vitronectin) or 60 minutes (laminin-1), washed three times in PBS and stained with Hoechst 33342 (1 µg/ml; Molecular Probes). The cells were micro-photographed using the 2× objective and the number of attached cells was counted using the "Easy Image Analysis" software (Tekno Optik). Statistical analysis was performed by ANOVA and Tukeys honestly significant difference (HSD) test. The standard deviation is based on the pooled variance. The results are shown in FIG. 9.

Experiment 12

Immunization of Rabbits to Raise 0119 Antibody

The 0119-antiserum was produced by immunizing rabbits with a 25 amino acid residue peptide with the following sequence: CRHSHNNNSSDLHPHKHHSHEQHPH (denoted 0119 peptide) (SEQ ID NO: 31). Residues 2-25 correspond to amino acid residues 321-344 of human HRGP. An N-terminal cysteine residue was added to the peptide to increase its stability and to allow coupling.

Experiment 13

Affinity Purification of 0119-reactive Proteins in Human Plasma a) Affinity Purification of 0119-antibodies:

The 0119 peptide was coupled to Sulfolink (Pierce) according to the manufacturer's protocol. Serum from 0119-immunized rabbits was incubated with peptide-coupled Sulfolink over night at 4° C. After incubation the beads were packed in a column (Polyprep, Biorad) and washed with PBS. Elution of bound material was performed with 4.6 M MgCl2; the eluate was subsequently dialyzed against PBS. Dialyzed material was precipitated over night at 4° C. with saturated ammonium sulfate solution at pH 7. Precipitated material was pelleted by low-speed centrifugation and the pellet was dissolved in PBS. The solution was dialyzed against PBS. Absorbance at 280 was read to estimate the protein concentration.

b) Coupling of Purified 0119-antibody to SEPHAROSE Column and Purification from Plasma:

The purified 0119-antibody was coupled to a HiTrap NHS-activated Sepharose column (Amersham Pharmacia Biotech) according to the manufacturer's protocol. Human plasma was diluted 1:10 with 0.2 M NaHCO$_3$, 0.5 M NaCl, pH 8.3 and applied to the column. After washing with the same buffer, bound material was eluted in 0.5 ml fractions with 100 mM glycin pH 2.7 and the pH of eluted material was adjusted to 7 using Tris-HCl, pH 8.5. Protein containing fractions were separated on SDS-PAGE and proteins visualized by silver-staining and immunoblotting using the 0119 antiserum.

The results are shown in FIG. 11.

Experiment 14

Synthetic Peptides

Procedure

Synthetic peptides were produced by Multiple Peptide Systems, San Diego Calif., USA, and dissolved in 1 mM ZnCl$_2$/0.5xPBS at a stock concentration of 1 mg/ml. The sequences of the peptides were as follows:

| Pep 8: | DLHPHKHHSHEQHPHG | (SEQ ID NO: 15) |
| Pep 9A: | KHHSHEQHPHGHHPHAHHPHEHDTHG | (SEQ ID NO: 16) |
| Pep 10: | AHHPHEHDTHRQHPHG | (SEQ ID NO: 18) |
| Pep 11A: | DLHPHEQHPHEHDTHG | (SEQ ID NO: 19) |

Some peptides were synthesized with an amidated carboxy terminus and an acetylated aminoterminus;

| Pep 12A: | Ac-AHHPHEHDTHRQHPH-NH2 | (SEQ ID NO: 21) |
| Pep 13A: | Ac-AHHPHEHDTH-NH2 | (SEQ ID NO: 23) |
| Pep 15A: | Ac-EHDTH-NH2 | (SEQ ID NO: 27) |

A migration assay was performed in a modified Boyden chamber as described earlier (Auerbach et al., 1991) using micropore polycarbonate filters (8 µm thick, 8 µm pore) coated with type-1 collagen solution at 100 µg/ml (Vitrogen 100, Collagen Corp). Primary bovine adrenal cortex capillary endothelial (BCE) cells were trypsinized and resuspended at a concentration of 7.5×10$^5$ cells/ml in Dulbecco's modified essential medium (Invitrogen) containing 0.25% BSA and Trasylol at 1000 KIE. The cell suspension was placed in the upper chamber. In the lower chamber below the filter was placed medium containing 0.25% BSA and when indicated, 10 ng/ml fibroblast growth factor (FGF-2; Peprotech). Recombinant HRGP produced in 293 cells, alternatively, synthetic peptides, all at a final concentration of 100 ng/ml (or as indicated), was placed in both chambers either alone or in combination with FGF-2. After 5 h at 37° C., the medium was removed and cells sticking to the filter were fixed in pure methanol and stained with Giemsa stain. The number of cells on the lower side of the filter was counted using an image analysis software (Easy Image Analysis) from TeknoOptik, Sweden. All samples were analyzed in series of at least six parallel wells for each treatment.

Results

The results of the chemotaxis assay, as described in the section above, are illustrated in Table 2 below.

TABLE 2

| Peptide | SEQ. ID.NO: | Amino acid sequence | Inhibition of chemotaxis |
|---|---|---|---|
| Pep 8 | NO.15 | DLHPHKHHSHEQHPHG | − |
| Pep 9A | NO:16 | KHHSHEQHPHGHHPHAHHPHEHDTHG | + |
| Pep 10 | NO:18 | AHHPHEHDTHRQHPHG | + |
| Pep 11A | NO:19 | DLHPHEQHPHEHDTHG | − |
| Pep 12A | NO:21 | Ac-AHHPHEHDTHRQHPH-NH$_2$ | + |
| Pep 13A | NO:23 | Ac-AHHPHEHDTH-NH$_2$ | + |
| Pep 15A | NO:27 | Ac-EHDTH-NH$_2$ | + |

As seen in table 2, Pep 9A, Pep 10, Pep 12A, Pep 13A and Pep 15A all inhibited chemotaxis, as compared to Pep 8 and Pep 11A.

Experiment 16

SDS-PAGE and Immunoblotting

Samples (see FIG. 10, experiment 13, and FIG. 11) were separated by SDS-PAGE and transferred to Hybond-C extra (Amersham Pharmacia Biotech). Immunoblotting was performed with the 0119 antibody. Proteins were visualized by a chemiluminescence detection system (Amersham Biosciences).

Experiment 17

Immunofluorescent Staining of Human Kidney

Human normal kidney tissue was obtained from the biobank at Uppsala University Hospital and used with the permission of the ethics commission of the University of Uppsala. Briefly, frozen sections of 6 µm were fixed for 15 minutes in ice-cold methanol, rehydrated for 5 min in PBS and then blocked in 3% bovine serum albumin for 1 h at room temperature. Thereafter, the sections were incubated for 2 h with affinity-purified 0119 antibodies, washed 15 min in PBS, and incubated with anti-rabbit-Fab2-Alexa 568 (1:1000 dilution; Invitrogen) and FITC-conjugated Ulex Europeus Agglutinin-1 (UEA-1; 1:200 dilution; Vector Laboratories) for 1 h at room temperature, followed by extensive washing in PBS. Finally, the sections were mounted in Fluoromount-G (Southern Biotechnology Associates) and analyzed using a LSM 510 META confocal microscope (Carl Zeiss). The results are shown in FIG. 12.

REFERENCES

1. Risau, W. (1997) Nature 386, 671-674.
2. Carmeliet, P. & Jain, R. K. (2000) Nature 407, 249-257.
3. Folkman, J. (1995) Nat Med 1, 27-31.
4. Hanahan, D. & Weinberg, R. A. (2000) Cell 100, 57-70.
5. Folkman, 3. (2000) in Cancer Medicine, 5th Edition, eds. Holland, J. F., Frei, E. I., Bast, R. C. J., Kufe, D. W., Pollock, R. E. & Weichselbaum, R. R. (B. C. Decker Inc, Ontario), pp. 132-152.
6. Kerbel, R. S. (2000) Carcinogenesis 21, 505-515.
7. Heimburger, N., Haupt, H., Kranz, T. & Baudner, S. (1972) Hoppe Seylers Z Physiol Chem 353, 1133-1140.
8. Drasin, T. & Sahud, M. (1996) Thromb Res 84, 179-188.
9. Hulett, M. D. & Parish, C. R. (2000) Immunol Cell Biol 78, 280-287.
10. Borza, D. B., Tatum, F. M. & Morgan, W. T. (1996) Biochemistry 35, 1925-1934.
11. Koide, T., Foster, D., Yoshitake, S. & Davie, E. W. (1986) Biochemistry 25, 2220-2225.
12. Kluszynski, B. A., Kim, C. & Faulk, W. P. (1997) J Biol Chem 272, 13541-13547.
13. Gorgani, N. N., Parish, C. R., Easterbrook Smith, S. B. & Altin, J. G. (1997) Biochemistry 36, 6653-6662.
14. Lijnen, H. R. & Collen, D. (1985) Ann N Y Acad Sci 556, 181-185.
15. Gorgani, N. N., Smith, B. A., Kono, D. H. & Theofilopoulos, A. N. (2002) J Immunol 169, 4745-4751.
16. Wennström, S., Landgren, E., Blume-Jensen, P. & Claesson-Welsh, L. (1992) J Biol Chem 267, 13749-13756.
17. Vernersson, M., Ledin, A., Johansson, J. & Hellman, L. (2002) Faseb J 16, 875-877.
18. Rylatt, D. B., Sia, D. Y., Mundy, J. P. & Parish, C. R. (1981) Eur J Biochem 119, 641-646.
19. Friedlander, M., Brooks, P. C., Shaffer, R. W., Kincaid, C. M., Varner, J. A. & Cheresh, D. A. (1995) Science 270, 1500-1502.
20. Dixelius, J., Larsson, H., Sasaki, T., Holmqvist, K., Lu, L., Engström, A., Timpl, R., Welsh, M. & Claesson-Weish, L. (2000) Blood 95, 3403-3411.
21. Workman, P., Balmain, A., Hickman, J. A., McNally, N. J., Rohas, A. M., Mitchison, N. A., Pierrepoint, C. G., Raymond, R., Rowlatt, C., Stephens, T. C. & et al. (1988) Lab Anim 22, 195-201.
22. Weibel, E. R. (1979) Stereological methods (Academic Press Inc, London).
23. Gundersen, H. J., Bendtsen, T. F., Korbo, L., Marcussen, N., Moller, A., Nielsen, K., Nyengaard, J. R., Pakkenberg, B., Sorensen, F. B., Vesterby, A. & et al. (1988) Apmis 96, 379-394.
24. Wassberg, E., Hedborg, F., Sköldenberg, E., Stridsberg, M. & Christofferson, R. (1999) Am J Pathol 154, 395-403.
25. Auerbach, R., Auerbach, W. & Polakowski, I. (1991) Pharmacol Ther 51, 1-11.
26. Hawighorst, T., Oura, H., Streit, M., Janes, L., Nguyen, L., Brown, L. F., Oliver, G., Jackson, D. G. & Detmar, M. (2002) Oncogene 21, 7945-7956.
27. O'Reilly, M. S., Holmgren, L., Chen, C. & Folkman, J. (1996) Nat Med 2, 689-692.
28. Zhang, J. C., Claffey, K., Sakthivel, R., Darzynkiewicz, Z., Shaw, D. E., Leal, J., Wang, Y. C., Lu, F. M. & McCrae, K. R. (2000) Faseb J 14, 2589-2600.
29. Juarez, J. C., Guan, X., Shipulina, N. V., Plunkett, M. L., Parry, G. C., Shaw, D. E., Zhang, J. C., Rabbani, S. A., McCrae, K. R., Mazar, A. P., Morgan, W. T. & Donate, F. (2002) Cancer Res 62, 5344-5350.
30. Simantov, R., Febbralo, M., Crombie, R., Asch, A. S., Nachman, R. L. & Silverstein, R. L. (2001) J Clin Invest 107, 45-52.
31. Lamb-Wharton R. J et al, (1993), Cellular Immunology, 152:544-555
32. Olsen H M et al (1996), Immunology, 88:198-206
33. Dayhoff, Schwartz, and Orcutt (1978) Atlas Protein Seq. Struc. 5:345-352
34. Henikoff and Henikoff (1992) Proc Natl Acad Sci USA 89(22):10915-9
35. Simon R J et al., PNAS (1992) 89(20), 9367-9371
36. Horwell D C, Trends Biotechnol. (1995) 13(4), 132-134
37. GCG program package (Devereux, J., et al., Nucleic Acid Research 12 (1):387 (1984)
38. BLASTP, BLASTN, and FASTA (Altschul, S. F., et al., Molec. Biol. 215: 403-410 (1990)
39. BLAST Manual, Altschul, S. F., et al., NCBI NLM NIH Bethesda, Md. 20894
40. Altschul, S. F., et al., J. Molec. Biol. 215:403-410 (1990)
41. "PCR Primer: A Laboratory Manual," Dieffenbach, C. and Dveksler, G., Cold Spring Harbor Laboratory Press, 1995
42. Sambrook et al, (1989) "Molecular Cloning," second edition, Cold Spring Harbor Laboratory, Plainview, N.Y., sections 7 7.52
43. Kolde T, Foster D, Odani S. The heparin-binding site(s) of histidine-rich glycoprotein as suggested by sequence homology with antithrombin III. FEBS Lett. 1986 Jan. 6; 194(2):242-4
44. Maniatis et al. (1989) Molecular Cloning: A Laboratory Manual, Cold Spring Harbor Laboratory, N.Y., pages 16.1-17.44
45. Hunter et al. (1962) Nature 144:945
46. David G S, Reisfeld R A. (1974) Protein iodination with solid state lactoperoxidase. Biochemistry. 13:1014-1021

47. Pain D, Surolia A. (1981) Preparation of protein A-peroxidase monoconjugate using a heterobifunctional reagent, and its use in enzyme immunoassays. J Immunol Methods. 40:219-230.
48. Nygren H. (1982) Conjugation of horseradish peroxidase to Fab fragments with different homobifunctional and heterobifunctional cross-linking reagents. A comparative study. J Histochem Cytochem. 30:407-412.
49. Kohler G, Milstein C. (1975) Continuous cultures of fused cells secreting antibody of predefined specificity. Nature 256:495-497.
50. Kosbor et al. (1983) Immunology Today 4:72
51. Cole et al. (1983) Proc. Natl. Acad. Sci. USA 80:2026
52. Cole et al. (1983) "Monoclonal Antibodies and Cancer Therapy", Alan R. Liss, Inc., pp. 77-96.
53. Green et al. (1994) Nature Genetics 7:13-21
54. Huse et al. (1989) Science, 246:12
55. Short Protocols in Molecular Biology, Chapter 11, Green Publishing Associates and John Wiley & Sons, Edited by Ausubel, F. M et al., 1992
56. Zola, Monoclonal Antibodies: A Manual of Techniques, pp. 147-158 (CRC Press, Inc., 1987)
57. Goeddel, Gene Expression Technology. Methods in Enzymology, vol. 185, Academic Press, San Diego, Calif. (1990).
58. Lijnen et al, Thromb Res 23, 121-131 (1981)

The invention claimed is:

1. A substantially pure anti-angiogenic polypeptide consisting of SEQ ID NO: 1 or SEQ ID NO: 2.

2. The polypeptide of claim 1, wherein the polypeptide consists of SEQ ID NO: 2.

3. The polypeptide of claim 1, wherein the polypeptide consists of SEQ ID NO: 1.

4. The polypeptide of claim 1, wherein said polypeptide is isolated from human HRGP.

5. The polypeptide of claim 1, wherein said polypeptide is isolated from proteolytically processed human HRGP purified from plasma.

6. The polypeptide of claim 1, wherein said polypeptide is recombinantly produced or isolated from recombinantly produced human HRGP.

7. The polypeptide of claim 1, wherein said polypeptide is synthetically produced.

8. The polypeptide of claim 1, wherein said polypeptide does not promote angiogenesis or does not bind to thrombospondin.

9. A pharmaceutical composition comprising an effective amount of the polypeptide of claim 1.

10. The pharmaceutical composition of claim 9, further comprising a pharmaceutically acceptable carrier.

11. The pharmaceutical composition of claim 9, further comprising an anti-angiogenic agent.

12. The pharmaceutical composition of claim 11, wherein said anti-angiogenic agent is selected from the group consisting of angiostatin, thrombostatin, endostatin, interferon-α, interferon-inducible factor 10, and platelet factor 4.

13. The pharmaceutical composition of claim 9, further comprising an anti-neoplastic agent.

14. The pharmaceutical composition of claim 13, wherein said antineoplastic agent is selected from the group consisting of taxol, cyclophosphamide, carboplatinum, cisplatinum, cisplatin, gancyclovir, camptothecin, paclitaxel, hydroxyurea, 5-azacytidine, 5-aza-2'-deoxycytidine, and suramin.

15. The pharmaceutical composition of claim 9, further comprising an anti-inflammatory agent.

16. The pharmaceutical composition of claim 15, wherein said antiinflammatory agent is selected from the group consisting of prednisone, a cox-2 inhibitor, ibuprofen and aspirin.

17. The pharmaceutical composition of claim 9, further comprising an effective amount of Zn2+.

18. A substantially pure anti-angiogenic polypeptide consisting of SEQ ID NO: 16, SEQ ID NO: 18, SEQ ID NO: 21, SEQ ID NO: 23, or SEQ ID NO: 27.

19. The substantially pure anti-angiogenic polypeptide of claim 18, wherein the polypeptide consists of SEQ ID NO: 16.

20. The substantially pure anti-angiogenic polypeptide of claim 18, wherein the polypeptide consists of SEQ ID NO: 18.

21. The substantially pure anti-angiogenic polypeptide of claim 18, wherein the polypeptide consists of SEQ ID NO: 21.

22. The substantially pure anti-angiogenic polypeptide of claim 18, wherein the polypeptide consists of SEQ ID NO: 23.

23. The substantially pure anti-angiogenic polypeptide of claim 18, wherein the polypeptide consists of SEQ ID NO: 27.

24. A pharmaceutical composition comprising an effective amount of the polypeptide of claim 18.

25. A method for inhibiting angiogenesis in a mammal, comprising administering the polypeptide of claim 1 to a mammal in need thereof.

26. A method for inhibiting angiogenesis in a mammal, comprising administering the polypeptide of claim 18 to a mammal in need thereof.

* * * * *

UNITED STATES PATENT AND TRADEMARK OFFICE
CERTIFICATE OF CORRECTION

| | | |
|---|---|---|
| PATENT NO. | : 7,662,388 B2 | Page 1 of 1 |
| APPLICATION NO. | : 10/563389 | |
| DATED | : February 16, 2010 | |
| INVENTOR(S) | : Welsh et al. | |

It is certified that error appears in the above-identified patent and that said Letters Patent is hereby corrected as shown below:

Title Page Item (56), References Cited, Other Publications, R. Simantov, et al. reference, please delete "antiagiogenic" and insert --antiangiogenic-- therefor;

Title Page Item (56), References Cited, Other Publications, Hulett M.D., et al. reference, please delete "histidide-rich" and insert --histidine-rich-- therefor;

Title Page Item (56), References Cited, Other Publications, D.J. Borza, et al. reference, please delete "histidine-roline-rich" and insert --histidine-proline-rich-- therefor;

Column 60, line 9 (Claim 17), please delete "Zn2+" and insert --$Zn^{2+}$-- therefor.

Signed and Sealed this

Twenty-fifth Day of May, 2010

David J. Kappos
*Director of the United States Patent and Trademark Office*